(12) United States Patent
Murao et al.

(10) Patent No.: US 8,716,439 B2
(45) Date of Patent: May 6, 2014

(54) METHOD OF PRODUCING PEPTIDE

(75) Inventors: Hiroshi Murao, Takasago (JP); Ken-ichiro Morio, Takasago (JP); Masaru Mitsuda, Takasago (JP)

(73) Assignee: Kaneka Corporation, Osaka (JP)

( * ) Notice: Subject to any disclaimer, the term of this patent is extended or adjusted under 35 U.S.C. 154(b) by 899 days.

(21) Appl. No.: 12/224,543

(22) PCT Filed: Jul. 31, 2006

(86) PCT No.: PCT/JP2006/315174
§ 371 (c)(1),
(2), (4) Date: Aug. 29, 2008

(87) PCT Pub. No.: WO2007/099656
PCT Pub. Date: Sep. 7, 2007

(65) Prior Publication Data
US 2009/0069538 A1   Mar. 12, 2009

(30) Foreign Application Priority Data
Mar. 1, 2006 (JP) ................... 2006-055094

(51) Int. Cl.
*A61K 38/00* (2006.01)

(52) U.S. Cl.
USPC ............. 530/344; 530/333; 530/338; 514/1.1

(58) Field of Classification Search
None
See application file for complete search history.

(56) References Cited

U.S. PATENT DOCUMENTS

| | | | |
|---|---|---|---|
| 5,516,891 A | 5/1996 | Siwruk et al. | |
| 5,874,532 A | 2/1999 | Pieken et al. | |
| 6,846,806 B2 * | 1/2005 | Priestley | 530/330 |
| 6,864,357 B2 | 3/2005 | Eggen et al. | |
| 7,776,966 B2 * | 8/2010 | Shibata et al. | 525/100 |
| 2003/0018164 A1 | 1/2003 | Eggen et al. | |
| 2009/0005506 A1 * | 1/2009 | Shibata et al. | 525/63 |

FOREIGN PATENT DOCUMENTS

| | | | |
|---|---|---|---|
| EP | 1 291 356 | 3/2003 | |
| EP | 1995254 A1 * | 11/2008 | C07K 1/02 |
| JP | 54-141704 | 11/1979 | |
| JP | 6-509821 | 11/1994 | |
| JP | 2002-511840 | 4/2002 | |
| JP | 2003-500415 | 1/2003 | |
| JP | 2003-55396 | 2/2003 | |
| JP | 2003-73396 | 3/2003 | |
| WO | 93/25571 | 12/1993 | |
| WO | 00/71569 | 11/2000 | |

OTHER PUBLICATIONS

Izumiya et al., "Pepuchido Gosei no Kiso to Jikken (Basic Concepts and Experiments of Peptide Synthesis)", Maruzen Co., Ltd. (1985) with partial English translation.
S. Nozaki et al., "Rapid Peptide Synthesis in Liquid Phase. Preparation of Angiotensin II and Delta-sleep-inducing peptide by the 'Hold-in-Solution' Method", Bull. Chem. Soc. Jpn., vol. 55, No. 7, pp. 2165-2168, 1982.
L. A. Carpino et al., "Rapid, Continuous Solution-Phase Peptide Synthesis: Application to Peptides of Pharmaceutical Interest", Organic Process Research & Development, vol. 7, pp. 28-37, 2003.
Extended European Search Report mailed Mar. 22, 2012 in corresponding European Application No. 06 78 2052.
Loffet, A. et al., "Rapid methods for the synthesis of peptides", Reactive Polymers, vol. 22, No. 3, Jun. 1, 1994, pp. 165-170.
Bodanszky, M. et al., "o-Nitrophenyl Esters of Benzyloxycarbonylamino Acids and Their Application in the Synthesis of Peptide Chains by the in situ Technique", Journal of Organic Chemistry, vol. 39, No. 4, Feb. 1, 1974, pp. 444-447.
Japanese Office Action entitled "Notice of Reasons for Refusal" (together with English translation) dispatched Jan. 10, 2012, in Japanese Patent Application No. 2008-502643.

* cited by examiner

*Primary Examiner* — Maury Audet
(74) *Attorney, Agent, or Firm* — Wenderoth, Lind & Ponack, L.L.P.

(57) ABSTRACT

The present invention is related to a method of producing a peptide, characterized in contacting a reaction mixture with a base after a condensation reaction to hydrolyze while a basic condition is maintained until a ratio of a remaining unreacted active ester of an acid component is decreased to 1% or less in a liquid phase peptide synthesis method. According to the invention, a target peptide of high purity can be simply and efficiently produced by a continuous liquid phase synthesis method. Further, the present invention is related to a method of producing a peptide, characterized in using an amide-type solvent immiscible with water in a liquid phase peptide synthesis method. According to the invention, various peptides can be produced by the liquid phase synthesis method without being restricted by the amino acid sequence of the target peptide.

7 Claims, No Drawings

SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Boc-modified; t-butoxycarbonyl (Boc) protecting
      group
<220> FEATURE:
<221> NAME/KEY: MISC_FEATURE
<222> LOCATION: (4)..(4)
<223> OTHER INFORMATION: OBn-modified; Bn: benzyl group

<400> SEQUENCE: 1

Gly Gly Phe Leu
1

<210> SEQ ID NO 2
<211> LENGTH: 5
<212> TYPE: PRT
<213> ORGANISM: Artificial Sequence
<220> FEATURE:
<223> OTHER INFORMATION: Synthetic construct
<220> FEATURE:

```
<221> NAME/KEY: MISC_FEATURE
<222> LOCATION: (1)..(1)
<223> OTHER INFORMATION: Tyr(Bn) modification; Tyr(Bn): O-benzyltyrosine
<220> FEATURE:
<221> NAME/KEY: MISC_FEATURE
<222> LOCATION: (5)..(5)
<223> OTHER INFORMATION: OBn-modified; Bn: benzyl group

<400> SEQUENCE: 2

Tyr Gly Gly Phe Leu
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: OBn-modified; Bn: benzyl group

<400> SEQUENCE: 3

Gly Gly Phe Leu
1

<210> SEQ ID NO 4
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Boc-modified; t-butoxycarbonyl (Boc) protecting
      group
<220> FEATURE:
<221> NAME/KEY: MISC_FEATURE
<222> LOCATION: (1)..(1)
<223> OTHER INFORMATION: Tyr(Bn) modification; Tyr(Bn): O-benzyltyrosine
<220> FEATURE:
<221> NAME/KEY: MISC_FEATURE
<222> LOCATION: (5)..(5)
<223> OTHER INFORMATION: OBn-modified; Bn: benzyl group

<400> SEQUENCE: 4

Tyr Gly Gly Phe Leu
1               5
```

METHOD OF PRODUCING PEPTIDE

This application is a U.S. national stage of International Application No. PCT/JP2006/315174 filed Jul. 31, 2006.

TECHNICAL FIELD

The present invention relates to a method of producing a peptide, which is capable of efficiently producing a peptide compound with high purity with a simple procedure.

BACKGROUND ART

A peptide is a compound composed of a plurality of amino acids condensed with one another through a peptide bond, and has various properties based on the amino acids as constituent components, such as hydrophilicity, hydrophobicity, acidity and basicity. Further, a peptide has an intrinsic conformation depending on an amino acid sequence. Because of these characteristics, a peptide has various functions such as expression of a bioactivity via an interaction with a protein or the like.

For example, a peptide compound having a bioactivity can be developed into a pharmaceutical product. At present, a large number of peptide pharmaceutical products have been approved and sold on the market. Therefore, an expectation of development of simple, efficient and widely used synthesis method of a peptide compound has been increased.

A peptide is synthesized by repeating a dehydration-condensation reaction between an amino group of one amino acid component and a carboxyl group of another amino acid component, i.e. a peptide chain elongation reaction, depending on the amino acid sequence of the peptide. Of the two amino acid components involved in this peptide bond formation, the component that provides the amino group is referred to as an amine component, and the component that provides the carboxyl group is referred to as an acid component.

In a chemical peptide synthesis method, an acid component is activated by any of various active ester methods or with a coupling reagent typified by dicyclohexylcarbodiimide (DCC), propanephosphonic anhydride (T3P) or the like, and is reacted with an amine component, thereby a peptide bond is formed. In the chemical synthesis method, a functional group which should not participate in a condensation reaction, such as a carboxyl group of an amine component or an amino group of an acid component, is protected; and a condensation reaction is carried out; and then, the protecting group for the N-terminal amino group of the resulting condensed product is removed to form a new amine component; so that the reaction is controlled in order to obtain a peptide having a desired amino acid sequence. In this chemical peptide synthesis method, there are mainly a solid phase method in which a peptide chain is elongated on a solid phase support and a liquid phase method in which a reaction is carried out in a liquid phase.

In the solid phase method, an amine component of which the C-terminal carboxyl group is protected in such a form that the C-terminal carboxyl group is bound to an insoluble solid phase support composed of, for example polystyrene, via a linker is used; a successive elongation reaction is carried out while the C-terminal carboxyl group is bound to the solid phase support; the C-terminal carboxyl group is cleaved from the solid phase support after a desired sequence is completed to obtain a target peptide. The full automation of the solid phase method is easy to be achieved, since various peptides can be synthesized almost independent of their sequences by the method.

However, it is generally difficult in the solid phase method to completely react all amine components on the solid phase support, since an inhomogeneous reaction of a solid-liquid two phase system is carried out and the reaction site of the amine component is sterically crowded on the solid phase support. When a part of amine components bound to the solid phase support remain in an unreacted state in the condensation reaction, it is necessary to completely react the amine components using a large excess of reagents such as an acid component and a coupling reagent.

Further, it is difficult in the solid phase method to monitor a reaction conversion ratio or a quality. In addition, the impure peptide cannot be removed at all until the desired sequence is completed and cleaved from the solid phase support, since the by-produced impure peptide is bound to the solid phase support together with the target peptide. It is generally difficult to remove the impure peptide, since the impure peptide has a similar property to that of the target peptide due to a common partial structure among the peptides. From the above reasons, the solid phase method is incomplete particularly as a method of synthesizing a peptide compound of high purity.

Furthermore, when the solid phase method is applied to the production of a peptide compound on an industrial scale, there is a restriction in terms of the production facility and the like; and a relatively expensive solid phase support and a large amount of reagents and a solvent are used; and also a large amount of waste is generated in proportion to the amount of the used reagent or solvent; therefore, a high cost is required for a raw material and waste liquid disposal. Accordingly, it is hard to say that the solid phase method is an economically advantageous method.

On the other hand, the liquid phase method is a method in which a condensation reaction for forming a peptide bond and a deprotection reaction for removing a protecting group for the N-terminal amino group of the resulting condensed product to form a new amine component are carried out in a liquid phase (solution) by using a protecting group capable of making the resulting condensed product soluble in a reaction solvent as a protecting group for a carboxyl group of an amine component. In the liquid phase method, an impure peptide can be removed by purification in the middle stage of the peptide chain elongation. However, when a side chain functional group of an amino acid is not protected, complicated purification procedures such as chromatography purification of an intermediate, a crystallization procedure and a crystal washing procedure with a plurality of solvent systems are required for the respective condensation steps (refer to Non-patent document 1). Further, even when an amino acid of which a side chain functional group is completely protected is used, the method has a disadvantage that an impure peptide is by-produced and the purity of the target peptide is decreased, since an active ester remaining in a solution cannot be completely decomposed (refer to Non-patent document 2).

From the above circumstances, development of a liquid phase peptide synthesis method in which purification procedures for an intermediate are omitted as much as possible and a target peptide with high purity can be obtained by a simple procedure is demanded. Recently, a continuous liquid phase peptide synthesis method in which the respective procedures for peptide synthesis are simplified while maintaining the purity of the target peptide high has been developed.

As one of the continuous synthesis methods, there is the following liquid phase synthesis method reported by Carpino et al. (refer to Non-patent document 3 and Patent document 1). In the method, after a peptide condensation reaction using an excess amount of an acid component of which the N-terminal amino group is protected by a 9-fluorenylmethyloxycarbonyl (Fmoc) group and an amine component of which the C-terminal carboxyl group is protected by a t-butyl group, an active ester remaining in the solution is converted to an amide form to make the active ester harmless using a scavenger such as tris-(2-aminoethyl)amine; and at the same time, the protecting group for the amino group of the active ester is removed. Further, the removal of the protecting group for the N-terminal amino group of the target condensed product is also allowed to proceed, and decomposition of the active ester and removal of the protecting group for the N-terminal amino group are completed at the same time by using the above-mentioned scavenger. A compound generated by this active ester decomposition reaction is easily removed into an aqueous layer by washing with a weakly acidic aqueous solution. By repeating said series of procedures, a target peptide compound of high purity can be continuously synthesized.

Further, in the DioRaSSP method by Diosynth (refer to Patent document 2) which is a similar continuous synthesis method, after condensation using an excess amount of an acid component of which the N-terminal amino group is protected by a benzyloxycarbonyl (Z) group and an amine component of which the C-terminal carboxyl group is protected by a t-butyl group, an active ester remaining in the solution is converted to an amide form to make the active ester harmless using β-alanine benzyl ester as a scavenger. The amide form generated by the active ester decomposition reaction is converted to a decomposed product with a high water solubility by removing both protecting groups at the N-terminus and the C-terminus in the deprotection reaction of the N-terminal amino group of the condensed product through the subsequent catalytic hydrogenation; therefore, the resulting decomposed product is easily removed into an aqueous layer by a washing procedure. By repeating said series of procedures, a target peptide of high purity can be continuously synthesized.

These methods are capable of obtaining a target peptide compound with relatively high purity while simplifying the complicated purification procedures in the respective condensation steps, which were the problems in the conventional liquid phase synthesis method. Further, the continuous liquid phase synthesis method can be said to have high usefulness in the chemical peptide synthesis.

However, a protecting group for a target peptide is restricted in both of the method by Carpino et al. and the DioRaSSP method by the type of a scavenger for decomposing an active ester. In addition, it is necessary to use an expensive amine or unnatural amino acid derivative as the scavenger. Accordingly, development of a method of decomposing an active ester, which can be more widely used and is excellent in economical efficiency without depending on the type of a protected amino acid to be used and further without using an expensive reagent, has been demanded.

It is ideal in the liquid phase method that a target peptide compound and intermediate peptide thereof are dissolved in a liquid phase, and it is preferred that at least such peptides are homogenously dispersed in a liquid phase medium. Even when an organic solvent solution of the peptides is in a state of an emulsion or a gel, a problem does not arise in a reaction and a post-treatment if the peptides are in a homogenously dispersed state in the liquid phase medium. On the other hand, when the peptide compounds are aggregated and formed into an aggregate or the like, a problem arises that an unreacted amine component is incorporated into the aggregate and the reaction is not completed or a liquid separation procedure at the time of a post-treatment cannot be carried out. Accordingly, it has been demanded in the liquid phase method to develop a widely used novel medium (solvent system) capable of homogenously dispersing a wide range of peptide compounds in a liquid phase medium independent of their amino acid sequences.

As described above, a widely used chemical synthesis method capable of efficiently synthesizing a peptide compound with high purity having a desired amino acid sequence has not been fully established. Accordingly, development of a method of efficiently decomposing an active ester which greatly affect the quality of a peptide and a solvent system with a high solubility for peptides which are suitable for the respective procedures such as liquid separation in a continuous liquid phase method have been particularly and strongly demanded.

Patent document 1: U.S. Pat. No. 5,516,891
Patent document 2: JP-A-2003-55396
Non-patent document 1: Izumiya et al., "Pepuchido Gosei no Kiso to Jikken" (Basic Concepts and Experiments of Peptide Synthesis), Maruzen Co., Ltd. (1985)
Non-patent document 2: Bull. Chem. Soc. Jpn., 55, 2165 (1982)
Non-patent document 3: Org. Proc. Res. Dev., 7, 28 (2003)

DISCLOSURE OF THE INVENTION

Problems to be Solved by the Invention

In view of the above circumstances, an object of the present invention is to provide a method of decomposing an active ester, which are widely used and simple and does not depend on the types of protecting groups for the N-terminal amino group and the C-terminal carboxyl group, and a continuous liquid phase peptide synthesis method which utilizes the decomposition method and is efficient and excellent in economical efficiency. Further, another object of the invention is to provide a solvent system with a high solubility for peptides, which can be applied also to the above-mentioned continuous liquid phase synthesis method and can dissolve various peptide compounds.

Means for Solving the Problems

The present inventors made intensive studies aiming at establishing a method of efficiently and surely decomposing an active ester without using a scavenger in order to achieve the above objects. As a result, the inventors found that it is an important control point to maintain the reaction system in a basic condition when an unreacted acid component active ester is decomposed by contacting the reaction mixture after a condensation reaction with a base, and thus, the method of decomposing an active ester of the present invention has been completed.

Further, the present inventors made intensive studies also for establishing a solvent system with a high solubility for peptides, which can be applied also to a continuous liquid phase synthesis method and can dissolve various peptide compounds. As a result, the inventors found that an amide-type solvent which has high hydrophobicity and is immiscible with water, has a high solubility for peptides and has an ideal property for a liquid phase synthesis method, particularly a continuous liquid phase synthesis method; and thus, the solvent system with a high solubility for peptides of the present invention has been established.

The present invention is a method of producing a peptide by a liquid phase synthesis method, characterized in comprising steps of:

Step A: a step of reacting an active ester of an acid component with an amine component to obtain a condensed compound;

Step B: a step of purifying the condensed compound by removing an impurity in a reaction mixture obtained in Step A;

Step C: a step of removing a protecting group for an N-terminal amino group of the condensed compound obtained in Step B; and Step D: a step of purifying the condensed compound deprotected at the N-terminal amino group by removing an impurity in a reaction mixture obtained in Step C, if necessary;

wherein, in Step B, the unreacted active ester of the acid component is hydrolyzed by contacting the reaction mixture obtained in Step A with a base and maintaining a basic condition until an amount of the remaining unreacted active ester of the acid component is decreased to 1% or less.

Further, the present invention is a method of producing a peptide by a liquid phase synthesis method, characterized in comprising steps of:

Step A: a step of reacting an active ester of an acid component with an amine component to obtain a condensed compound;

Step B: a step of purifying the condensed compound by removing an impurity in a reaction mixture obtained in Step A;

Step C: a step of removing a protecting group for an N-terminal amino group of the condensed compound obtained in Step B; and Step D: a step of purifying the condensed compound deprotected at the N-terminal amino group by removing an impurity in a reaction mixture obtained in Step C, if necessary;

wherein, an amide-type solvent immiscible with water is used in at least one of the steps.

Effect of the Invention

According to the method of producing a peptide of a first invention of the present application, the active ester remaining in the solution after the condensation reaction can be decomposed by a simple and efficient method without using an expensive scavenger which has been used in a conventional continuous liquid phase synthesis method. In the case where the active ester remaining in the solution is decomposed so as to decrease the amount of the active ester to 1% or less, the by-production of an impure peptide compound is markedly reduced and the target peptide compound with high purity can be obtained in the subsequent peptide elongation reaction; therefore, a peptide compound with high purity having a desired amino acid sequence can be produced industrially advantageously.

Further, according to the method of producing a peptide of a second invention of the present application, the application range of the number of amino acids and the amino acid sequence in the liquid phase peptide synthesis method can be expanded.

BEST MODE FOR CARRYING OUT THE INVENTION

Hereinafter, the present invention is described in detail.

The peptide according to the present invention is a compound having a structure in which a plurality of amino acids is condensed with one another by forming an acid amide bond, i.e. a peptide bond between an amino group and a carboxyl group. The amino acid is not particularly limited as long as the amino acid is a compound having one or more amino groups and carboxyl groups, respectively, in one molecule. Of the two amino acid components involved in the peptide bond formation, the component that provides the carboxyl group is referred to as an acid component, and the component that provides the amino group is referred to as an amine component.

The acid component according to the present invention is not particularly limited and any of a variety of amino acid derivatives can be used as the acid component. Further, a peptide compound in which an amino group of an amino acid derivative is further condensed with another amino acid through a peptide bond can also be used. When a target peptide compound has, for example, an acyl-type substituent as a protecting group for an amino group at the N-terminus, a desired acyl group can also be introduced by using a carboxylic acid derivative corresponding to the acyl-type substituent in place of an amino acid derivative as the acid component.

The amine component according to the present invention is not particularly limited and any of a variety of amino acid derivatives can be used. Further, a peptide compound in which a carboxyl group of the amino acid derivative is further condensed with another amino acid through a peptide bond can also be used. In addition, a condensed product obtained by a condensation reaction is also one of the types of peptide compounds, and can be used as the amine component for a further elongation reaction (a condensation reaction) after deprotection of the N-terminus. When a target peptide compound has, for example, an amide-type substituent as a protecting group for a carboxyl group at the C-terminus, a desired amide group can also be introduced by using an amine derivative corresponding to the amide-type substituent in place of an amino acid derivative as the amine component.

The protecting group for the N-terminal amino group in the acid component and the protecting group for the C-terminal carboxyl group in the amine component cooperate for forming a desired peptide bond. Therefore, a combination of the protecting groups for the N-terminal amino group and the C-terminal carboxyl group is restricted to a certain degree. That is, when a peptide chain is not further elongated, the protecting group for the N-terminal amino group in the acid component is not particularly restricted; however, when a peptide chain is further elongated, it is necessary to remove the protecting group for converting the condensed product to the new amine component. Such a protecting group is referred to as a temporary protecting group. On the other hand, the protecting group for the C-terminal carboxyl group in the amine component is required to be retained until a desired amino acid sequence is completed without being removed even under the condition for the deprotection at the N-terminal amino group of the condensed product such that the amine component does not participate in the formation of the peptide bond by behaving as the acid component. Such a protecting group is referred to as a semipermanent protecting group.

Examples of the protecting group for the C-terminal carboxyl group in the amine component may include an ester-type protecting group, an amide-type protecting group and a hydrazide-type protecting group described in "Pepuchido Gosei no Kiso to Jikken" (Basic Concepts and Experiments of Peptide Synthesis), Maruzen Co., Ltd. (1985), "Protective Groups in Organic Synthesis, the third edition", John Willy & Sons Inc. (1999) and the like.

As the ester-type protecting group, a substituted or unsubstituted alkyl ester and a substituted or unsubstituted aralkyl ester are preferably used. As the substituted or unsubstituted alkyl ester, a methyl ester, an ethyl ester, a t-butyl ester, a cyclohexyl ester, a trichloroethyl ester, a phenacyl ester and the like are preferably used. As the substituted or unsubstituted aralkyl ester, a benzyl ester, a p-nitrobenzyl ester, a p-methoxybenzyl ester, a diphenylmethyl ester, a 9-fluorenylmethyl (Fm) ester, a 4-picolyl (Pic) ester and the like are preferably used.

As the amide-type protecting group, a primary amide such as an unsubstituted amide, an N-methyl amide, an N-ethyl amide and an N-benzyl amide; a secondary amide such as an N,N-dimethyl amide, a pyrrolidinyl amide and a piperidinyl amide and the like are preferably used.

As the hydrazide-type protecting group, an unsubstituted hydrazide, N-phenylhydrazide, N,N'-diisopropylhydrazide and the like are preferably used.

It is necessary to use an appropriate protecting group as the protecting group for the C-terminal carboxyl group described above under the restriction related to the combination with the protecting group for the N-terminal amino group described below. It is only necessary that the protecting group does not permit the carboxyl group to participate in the peptide bond formation by behaving as the acid component. For example, when a target peptide compound is an ester-type, an amide-type or a hydrazide-type derivative, the target peptide compound can also be synthesized without accompanying a deprotection of the protecting group for the C-terminal carboxyl group by using an appropriate protecting group for the N-terminal amino group to a desired protecting group as a substituent at the C-terminus introduced in advance.

The combination of the protecting groups for the N-terminal amino group and the C-terminal carboxyl group is not particularly limited as long as the protecting group for the N-terminal amino group is stable in the condensation reaction and also the protecting group for the C-terminal carboxyl group is stable in the condensation reaction and a deprotection condition for removal of the protecting group for the N-terminal amino group. Examples of the protecting group for the N-terminal amino group that satisfy the above-mentioned condition for the combination may include an urethane-type protecting group, an acyl-type protecting group and a sulfonyl-type protecting group described in "Pepuchido Gosei no Kiso to Jikken" (Basic Concepts and Experiments of Peptide Synthesis), Maruzen Co., Ltd. (1985), "Protective Groups in Organic Synthesis, the third edition", John Willy & Sons Inc. (1999) and the like.

In general, the urethane-type protecting group are preferred, since racemization of an amino acid is unlikely to be caused, introduction of the protecting group is relatively easy, and selective deprotection is easy. Specific examples of the urethane-type protecting group include branched alkyloxycarbonyl groups such as a t-butoxycarbonyl (Boc) group and an isobornyloxycarbonyl (Iboc) group; aralkyloxycarbonyl groups such as a benzyloxycarbonyl (Z) group, a p-nitrobenzyloxycarbonyl group, a p-biphenylisopropyloxycarbonyl (Bpoc) group and a 9-fluorenylmethyloxycarbonyl (Fmoc) group. Among them, the following protecting groups which have given satisfactory results in a chemical peptide synthesis method are preferred.

Firstly, a t-butoxycarbonyl (Boc) group can be exemplified as the protecting group. The Boc group is an amino group protecting group which can be removed under a relatively mild acidic condition. The Boc group can be removed even under a condition in which water is prohibited as long as the condition is an acidic condition. Therefore, it is also possible to selectively remove the Boc group while, for example, the ester-type protecting group for the carboxyl group which is subject to hydrolysis under an acidic condition is remained.

The protecting group for the C-terminal carboxyl group which can be combined with the Boc group is not particularly limited, and a protecting group which is stable under the condition for removal of the Boc group can be selected from the above-mentioned ester-type protecting group, amide-type protecting group, hydrazide-type protecting group and the like. As the ester-type protecting group, for example, a methyl ester, an ethyl ester, a substituted or unsubstituted benzyl ester and the like are preferably used. Among them, a substituted or unsubstituted benzyl ester is particularly preferably used, since the ester is relatively stable against hydrolysis under a basic condition and can be selectively removed under a mild condition.

Subsequently, a benzyloxycarbonyl (Z) group can be exemplified as the protecting group. The Z group is an amino group protecting group which can be removed under a relatively mild catalytic reduction condition.

The protecting group for the C-terminal carboxyl group which can be combined with the Z group is not particularly limited, and a protecting group which is stable under the condition for removal of the Z group can be selected from the ester-type protecting group, amide-type protecting group, hydrazide-type protecting group and the like. As the ester-type protecting group, for example, a methyl ester, an ethyl ester, a t-butyl ester and the like are preferably used. Among them, a t-butyl ester is particularly preferably used, since the ester is relatively stable against hydrolysis under a basic condition.

Finally, a 9-fluorenylmethyloxycarbonyl (Fmoc) group can be exemplified as the protecting group. The Fmoc group is an amino group protecting group which can be removed under a relatively mild basic condition.

The protecting group for the C-terminal carboxyl group which can be combined with the Fmoc group is not particularly limited, and a protecting group which is stable under the condition for removal of the Fmoc group can be selected from the above-mentioned ester-type protecting group, amide-type protecting group, hydrazide-type protecting group and the like. As the ester-type protecting group, for example, a t-butyl ester, a substituted or unsubstituted benzyl ester and the like are preferably used. Among them, a substituted or unsubstituted benzyl ester is particularly preferably used, since the ester is relatively easy to be synthesized.

Among the urethane-type protecting group, the Boc group is particularly preferably used on the grounds such that the Boc group is very stable in a condensation reaction and an active ester decomposition reaction, and a deprotection reaction thereof is easy.

The acid component and the amine component to be used in the present invention have a functional group with an activity for a reaction of forming a peptide bond such as an amino group, a carboxyl group, a hydroxy group or the like in many cases in addition to the amino group, the carboxyl group or the like involved in the peptide bond formation. These functional groups are referred to as a side chain functional group in distinction from the amino group and the carboxyl group for forming a peptide bond in the main chain. It is not always necessary to protect the side chain functional group unless the essential feature of the invention is not impaired. However, it is generally preferable to protect the side chain functional group is by an appropriate protecting group in order to prevent an undesired side reaction at the time of formation of a peptide bond through a condensation reaction and also at the time of deprotection reaction at the N-terminal amino group.

The protecting group for the side chain functional group is also restricted to a certain degree in terms of a combination with the protecting group for the N-terminal amino group like the above-mentioned protecting group for the C-terminal carboxyl group in the amine component. That is, the protecting group for the side chain functional group is required to be retained until a desired amino acid sequence is completed without being removed even under the condition for the deprotection at the N-terminal amino group. The protecting group is not particularly limited as long as the side chain functional group does not cause an undesired side reaction at the time of formation of a peptide bond through a condensation reaction and also at the time of deprotection reaction at the N-terminal amino group. For example, when the target peptide compound is a compound in which the side chain functional group is protected by a specific protecting group, the target peptide compound can also be synthesized without removing the protecting group for the side chain functional group by introducing a desired protecting group (substituent) at the side chain functional group of a corresponding acid component in advance and combining the above-mentioned protecting group with an appropriate protecting group for the N-terminal amino group.

The protecting group for the side chain functional group is not particularly limited as long as the protecting group is stable under a condition for removal of the protecting group (temporary protecting group) for the N-terminal amino group. The examples of the protecting group for the side chain functional group may include protecting groups described in "Pepuchido Gosei no Kiso to Jikken" (Basic Concepts and Experiments of Peptide Synthesis), Maruzen Co. Ltd. (1985), "Protective Groups in Organic Synthesis, the third edition", John Willy & Sons Inc. (1999) and the like.

When the side chain functional group is a carboxyl group, examples of the protecting group may include an ester-type protecting group, an amide-type protecting group and a hydrazide-type protecting group, which are the same protecting groups as the above-mentioned protecting group for the C-terminal carboxyl groups in the amine component.

When the side chain functional group is an amino group, examples of the protecting group may include an urethane-type protecting group, an acyl-type protecting group and a sulfonyl-type protecting group. As the urethane-type protecting group, for example, a methoxycarbonyl group, an ethoxycarbonyl group, a Boc group, a Z group and the like are preferably used. When the protecting group for the N-terminal amino group is a Boc group, a methoxycarbonyl group, an ethoxycarbonyl group, a Z group and the like are preferably used as the protecting group for the amino group as the side chain functional group. Among them, the Z group is particularly preferably used, since the Z group can be selectively removed under a hydrolysis condition using hydrogen gas or a formic acid compound as a hydrogen donor. When the protecting group for the N-terminal amino group is a Z group or an Fmoc group, a methoxycarbonyl group, an ethoxycarbonyl group, a Boc group and the like are preferably used as the protecting group for the side chain functional group. Among them, the Boc group is particularly preferably used, since the Boc group can be selectively removed under a relatively mild acidic condition.

As the acyl-type protecting group, for example, a formyl group, an acetyl group, a trifluoroacetyl group and the like are preferably used.

As the sulfonyl-type protecting group, for example, a p-toluenesulfonyl (Ts) group, a p-tolylmethanesulfonyl group, a 4-methoxy-2,3,6-trimethylbenzenesulfonyl group and the like are preferably used.

As also for the side chain functional group other than the above-mentioned side chain functional groups, a protecting group which is stable under the condition for removal of the protecting group (temporary protecting group) for the N-terminal amino group can be also selected and used.

The side chain functional group may be deprotected after a desired peptide bond is formed, if necessary.

Subsequently, the method of producing a peptide of a first invention of the present application is described. A first invention of the present application is a method of producing a peptide by a liquid phase synthesis method, characterized in comprising steps of:

Step A: a step of reacting an active ester of an acid component with an amine component to obtain a condensed compound;

Step B: a step of purifying the condensed compound by removing an impurity in a reaction mixture obtained in Step A;

Step C: a step of removing a protecting group for an N-terminal amino group of the condensed compound obtained in Step B; and Step D: a step of purifying the condensed compound deprotected at the N-terminal amino group by removing an impurity in a reaction mixture obtained in Step C, if necessary;

wherein, in Step B, the unreacted active ester of the acid component is hydrolyzed by contacting the reaction mixture obtained in Step A with a base and maintaining a basic condition until an amount of the remaining unreacted active ester of the acid component is decreased to 1% or less.

First, Step A is described. Step A is a step of forming a peptide bond by reacting an acid component active ester with an amine component. Not only an embodiment in which separately prepared acid component active ester and amine component are reacted with each other, but also an embodiment in which an acid component is converted to an active ester in a system containing both of the acid component and the amine component, and subsequently the resulting acid component active ester is reacted with the amine component are included in this step.

In general, the electrophilicity of a carbonyl carbon is increased by converting the acid component to the acid component active ester described below to accelerate the reaction in the peptide synthesis.

The acid component active ester according to the present invention represents a compound in which an electron-attracting substituent capable of increasing the electrophilicity of the carbonyl carbon is introduced in place of the hydroxy group of the carboxyl group of the acid component. Hereinafter, such an electron-attracting substituent capable of increasing the electrophilicity of the carbonyl carbon is referred to as an activating substituent. Further, a reagent to be converted to the activating substituent by being reacted with the carboxyl group of the acid component is referred to as an activating reagent.

The activating substituent to be introduced in place of the hydroxy group is not particularly limited, and examples of the activating substituent may include a substituted aryloxy group, a substituted or unsubstituted arylthioxy group, a group obtained by removing a hydrogen atom from a hydroxy group of a hydroxylamine compound, and a group obtained by removing a hydrogen atom from a carboxyl group of an organic acid (a so-called mixed acid anhydride is formed).

As the substituted aryloxy group, a group having an electron-attracting group such as a p-nitrophenoxy group (ONp), a 2,4-dinitrophenoxy group, a 1,3,5-trichlorophenoxy group, a pentachlorophenoxy group and a pentafluorophenoxy group is preferably used. Among them, a p-nitrophenoxy group is particularly preferably used, since the synthesis of the corresponding active ester is relatively easy, and the crystallization property and preservation property are good.

As the substituted or unsubstituted arylthioxy group, a phenylthioxy group, a p-nitrophenylthioxy group and the like are preferably used.

Examples of the hydroxylamine compound may include 1-hydroxybenzotriazole (HOBt), 1-hydroxy-7-azabenzotriazole (HOAt), 3-hydroxy-4-oxo-3,4-dihydro-1,2,3-benzotriazine (HOObt), N-hydroxysuccinimide (HONSu), N-hydroxyphthalimide and N-hydroxypiperidine. Examples of the group obtained by removing a hydrogen atom from a hydroxy group of the above hydroxylamine compound include a 1H-benzotriazol-1-yloxy (OBt) group, a 1H-7-azabenzotriazol-1-yloxy (OAt) group, a 4-oxo-3,4-dihydro-1,2,3-benzotriazine-3-yloxy (OObt) group, a succinimidyloxy (ONSu) group, a phthalimidyloxy group and a piperidin-1-yloxy group, respectively. Among them, an OBt group, an OAt group, an OObt group, an ONSu group and the like are particularly preferably used.

The organic acid is not particularly limited, but a monoalkyl carbonate, i.e. a monocarboxylic acid, or an organic acid with large steric hindrance is preferably used in order to prevent a side reaction. Examples of the monoalkyl carbonate may include monomethyl carbonate, monoethyl carbonate and monoisobutyl carbonate. Examples of the organic acid with large steric hindrance may include isovaleric acid and pivalic acid.

As the activating substituent, the group obtained by removing a hydrogen atom from a hydroxy group of a hydroxylamine compound and the group obtained by removing a hydrogen atom from a carboxyl group of an organic acid are preferred, since a decomposed product by hydrolyzing a remaining active ester after a condensation reaction in a basic condition is soluble in water and can be easily removed by washing with an aqueous solution. Particularly, the group obtained by removing a hydrogen atom from a hydroxy group of a hydroxylamine compound is preferably used.

A method of preparing the acid component active ester is not particularly limited, and the acid component active ester may be obtained from the acid component using a known method. Hereinafter, an OBt ester which is most frequently used in peptide synthesis is picked up and preparation method thereof is described as one example.

The OBt ester is generally prepared by dehydration-condensation of the acid component and HOBt serving as the activating reagent. As a condensing agent for accelerating this dehydration-condensation, a carbodiimide compound is preferably used. The carbodiimide compound condensates the acid component and HOBt; and at the same time, the carbodiimide compound itself is converted to a urea derivative. For example, when N,N'-dicyclohexylcarbodiimide (DCC) is used as the carbodiimide compound, dicyclohexylurea (DCUrea) which is hardly soluble in a reaction solvent is by-produced, and the by-product can be removed from the soluble active ester by a solid-liquid separation procedure. On the other hand, when a water-soluble carbodiimide (WSC) compound typified by 1-(3-dimethylaminopropyl)-3-ethylcarbodiimide hydrochloride (EDC) is used, a water-soluble urea derivative such as N-(3-dimethylaminopropyl)-N'-ethylurea (EDUrea) is by-produced, and the by-product can be removed by aqueous washing such as dilute acid washing. The acid component active ester prepared as described above is subsequently reacted with the amine component to form a peptide bond by a substitution reaction.

The active ester prepared using the carbodiimide compound may be isolated once, or the amine component is added to a mixture of HOBt and the acid component in advance and a carbodiimide compound is allowed to act on the mixture, thereby an OBt ester is prepared in the reaction system and the resulting OBt ester may be allowed to directly react with the amine component.

Further, the activating reagent for preparing an OBt ester without using the carbodiimide compound is also known. For example, the acid component is converted to a corresponding OBt ester in the reaction system, and the resulting OBt ester and the amine component can be efficiently dehydrated and condensated by allowing an activating reagent such as 1H-benzotriazol-1-yloxy-tris-dimethylamino-phosphonium hexafluorophosphate (BOP), 1H-benzotriazol-1-yloxy-tris-pyrrolidino-phosphonium hexafluorophosphate (PyBOP), 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU) or the like to directly act on a mixture of the acid component and the amine component.

Subsequently, a condition for the condensation reaction of the acid component active ester and the amine component is described. The used amount of the reagents to be used in this reaction is not particularly limited; however, it is necessary to completely react the amine component which is difficult to be removed if the component remains; therefore, it is generally preferred that the reagents other than the amine component are used in an excess amount relative to the amine component.

When the used amount of the acid component active ester is based on the amine component, the lower limit is generally 1.0 molar times or more, preferably 1.1 molar times or more, and more preferably 1.2 molar times or more. As the used amount of the acid component active ester is larger, the reaction rate is increased; however, it is very hard to remove the excess acid component at the time of a post-treatment. Therefore, the upper limit of the used amount is 10 molar times or less, preferably 3 molar times or less, and more preferably 1.5 molar times or less.

As described above, the acid component active ester may be prepared in the reaction system, or the separately prepared acid component active ester may be used. When the acid component active ester is prepared in the reaction system, the order of addition of the amine component, the acid component, the activating reagent and the condensing agent is not particularly limited; generally the acid component and the activating reagent to the amine component are added in advance, and then the condensing agent is added thereto. It is particularly preferable to use the method of preparing the active ester in the reaction system in this manner, in the case where HOBt, HOAt, HOObt or the like is used as the activating reagent. Hereinafter, the used amount of the respective components is described.

In the case where the used amount of the acid component is based on the amine component, the lower limit is generally 1.0 molar times or more, preferably 1.1 molar times or more, and more preferably 1.2 molar times or more. As the used amount of the acid component is larger, the reaction rate is increased; however, it is very hard to remove the excess acid component at the time of a post-treatment. Therefore, the upper limit of the used amount is 10 molar times or less, preferably 3 molar times or less, and more preferably 1.5 molar times or less.

In the case where the used amount of the activating reagent is based on the acid component, the lower limit is generally 1.0 molar times or more, preferably 1.1 molar times or more, and more preferably 1.2 molar times or more. As the used amount of the activating reagent is larger, the reaction rate is increased; however, it is very hard to remove the excess acid component at the time of a post-treatment. Therefore, the upper limit of the used amount is 10 molar times or less, preferably 3 molar times or less, and more preferably 1.8 molar times or less.

In the case where the used amount of the condensing agent is based on the acid component, the lower limit is generally 1.0 molar times or more, preferably 1.1 molar times or more, and more preferably 1.2 molar times or more. With regard to the upper limit of the used amount, 20 molar times is the upper limit of the used amount thereof, since the reaction can be sufficiently completed with 20 molar times of the used amount. The upper limit of the used amount is preferably 10 molar times or less, more preferably 5 molar times or less, and further more preferably 2 molar times or less.

The reaction solvent to be used in the condensation reaction is not particularly limited as long as the reaction solvent is essentially inert to the acid component, the amine component and the active ester or the respective reagents to be used in this reaction such as the activating reagent and the condensing agent. Examples of the reaction solvent may include aliphatic hydrocarbons such as hexane and heptane; aromatic hydrocarbons such as toluene and xylene; halogenated hydrocarbons such as dichloromethane, chloroform, 1,2-dichloroethane and chlorobenzene; ethers such as tetrahydrofurane, 1,4-dioxane, t-butylmethyl ether and diisopropyl ether; fatty acid esters such as methyl acetate, ethyl acetate and isopropyl acetate; aprotic polar solvents miscible with water such as acetonitrile, N,N-dimethylformamide (DMF) and dimethyl sulfoxide (DMSO); and aprotic polar solvents immiscible with water such as N,N-di-n-propylformamide and N,N-dibutylformamide (DBF).

Among them, halogenated hydrocarbons, fatty acid esters and aprotic polar solvents, which have a relatively high solubility for the respective reagents to be used in this reaction and a peptide compound, are preferably used. As the halogenated hydrocarbons, dichloromethane and chlorobenzene are particularly preferred. As the fatty acid esters, ethyl acetate is particularly preferred. As the aprotic polar solvents, DBF, DMF and DMSO are particularly preferred, and above all, DBF which is an aprotic polar solvent immiscible with water is preferred. As the solvent, particularly preferred are dichloromethane, chlorobenzene and DBF. These solvents may be used alone or by mixing two or more kinds. When the solvents are used by mixing two or more kinds, the mixing ratio thereof is not particularly limited.

Further, water may be allowed to coexist in these solvents. It is particularly preferable to coexist water, when a water-soluble carbodiimide such as EDC is used as the condensing agent. Since a water-soluble urea derivative can be dissolved or dispersed by the coexistence of water, while a by-produced water-soluble urea derivative such as EDUrea may be aggregated or solidified thereby causing deterioration of the fluidity of the reaction mixture and also preventing the reaction from proceeding smoothly in some cases.

The term "immiscible with water" as used herein represents the case that the mixture is separated into two layers, when the solvent is mixed with an equal volume of water at 20° C. and the resulting mixture is left stand.

The reaction temperature of this reaction is not particularly limited as long as the reaction temperature is not lower than the solidification temperature of the reaction mixture and not higher than the boiling point of the reaction mixture. However, in general, the reaction temperature is preferably 40° C. or lower and more preferably 30° C. or lower, since there is a tendency that an unfavorable side reaction is increased, as the reaction temperature is higher. In particular, when the acid component active ester is prepared in the reaction system, the condensing agent is added to a mixture composed of the amine component, the acid component and the activating reagent. It is preferred that the temperature is set as low as possible. For example, the temperature is preferably set to about 0 to 10° C., when water is contained in the reaction system.

The reaction concentration for this reaction is not particularly limited as long as the respective components such as the acid component, the amine component and the condensed peptide compound are dissolved or at least in a homogenously dispersed state. The reaction concentration cannot be uniformly specified, since the reaction concentration is affected by the types of the solvent and the above-mentioned respective components as solutes, the used amount thereof, the reaction temperature and the like. However, the condensation reaction can be generally carried out under a condition that the organic solvent in an amount of 4 to 50 times volume relative to the weight of the amine component is used. The condition corresponds to a condition that the amine component concentration in the reaction mixture is about 2 to 25%.

In this step, the condensation reaction can proceed quantitatively. The reaction conversion ratio in the condensation reaction can be expected to be at least 99% or more, generally 99.5% or more, preferably 99.9% or more.

Subsequently, Step B is described. Step B is a step of purifying the condensed product by removing an impurity contained in the reaction mixture obtained in Step A. This step is an important step in a liquid phase synthesis method of a peptide compound with high purity. In Step B, an impurity existed in the reaction mixture such as the unreacted acid component active ester, which would cause a by-reaction in subsequent steps, is removed directly or after decomposition. Examples of the specific procedure of this step include decomposition, extraction and washing, and crystallization of the unreacted acid component active ester. In general, these procedures can be carried out in combination with one another as needed, and particularly, decomposition and removal of the remaining acid component active ester are important. The first invention of the present application is characterized in that the acid component active ester is decomposed under a specific condition.

In the conventional liquid phase peptide synthesis method, basic washing with an aqueous solution of sodium hydrogen carbonate or sodium carbonate and acidic washing with an aqueous solution of citric acid or potassium hydrogen sulfate are carried out as a post-treatment of the condensation reaction. It is assumed that the above-mentioned active ester is decomposed and removed by this aqueous washing procedure. However, as a result of study about the conventional method by the present inventors, it was confirmed that the decomposition and removal of the active ester were not sufficient in many cases.

The present inventors found that the ease of decomposition of the active ester depends largely on the types of the acid component constituting the active ester and a coexisting condensed product of a peptide compound (an intermediate), as a result of intensive studies of the above decomposition of the active ester. Further, the present inventors found that the pH of an alkaline aqueous solution layer used for the decomposition is decreased as the decomposition of the active ester proceeded, and further the decomposition reaction does not proceed when the pH falls below a specific pH value.

The first invention of the present application was completed on the basis of the above-mentioned finding, and is characterized in that the amount of the remaining unreacted active ester is decreased to 1% or less with maintaining the reaction system in a basic condition, when the unreacted acid component active ester is decomposed by contacting the reaction mixture obtained in Step A with a base. The terms "a basic condition" as used herein means a pH condition which allows the decomposition of the acid component active ester to preferably proceed.

The pH required for allowing the decomposition of the acid component active ester to preferably proceed can be easily specified by the following manner. When, for example, a 5% aqueous sodium carbonate solution is added as the base to the reaction mixture, the active ester is not sufficiently decomposed and remains therein in many cases. When the base is added little by little to the reaction mixture in which the active ester remains while measuring the pH of the mixture, at first the pH is increased according to the addition amount of the above; however, a phenomenon in which the pH increased by the addition of the base begins to decrease immediately on reaching a certain pH can be observed. The addition of the base is stopped when this decrease of pH is observed, and the pH is measured every 10 minutes immediately thereafter. The pH at which the degree of decrease of pH becomes 0.1 or less is the pH required for allowing the decomposition of the active ester to preferably proceed in the reaction system. According to said procedure, the pH of the aqueous layer required for allowing the decomposition of the active ester to proceed depending on the type of the acid component constituting the active ester, a coexisting condensed product of a peptide compound (an intermediate) and the solvent can be specified as a control value.

In the actual production, it is preferred that while the pH of the reaction mixture is confirmed, the base is added until the pH is not decreased any more, or that the pH required for allowing the decomposition of the active ester to proceed, which confirmed in advance in the above-mentioned manner, is specified as a control value, and the pH is adjusted to and maintained at the control value or higher by adding the base. With regard to the pH measurement, the pH of the reaction mixture may be directly measured, or the pH of the alkaline aqueous solution layer added for the decomposition of the active ester may be measured. It is generally preferable to maintain the pH at 10.0 or higher; while it is difficult to uniformly specify the control value of the pH, since, as described above, the pH required for allowing the decomposition of the active ester to proceed greatly varies depending on the types of the acid component constituting the active ester and the coexisting condensed product of a peptide compound (an intermediate). The pH is more preferably 10.5 or higher, and further more preferably 11.0 or higher. In general, as the pH is higher, the decomposition reaction proceeds more promptly. However, it is preferred that the upper limit of the pH should be specified according to the balance with the efficiency of the decomposition reaction, since the used amount of the base increases exponentially with the pH value and the use of excess base is not efficient. It is also difficult to uniformly specify the upper limit of the pH; however, the pH is preferably maintained at 13.0 or lower. In general, the decomposition of the active ester sufficiently proceeds even at a pH of 12.0 or lower.

Alternatively, the pH can also be maintained at the control value or higher by removing the aqueous layer of which the pH as decreased as the decomposition of the active ester proceeds by liquid separation and freshly adding an aqueous solution of the base to the residue. This procedure is so-called repeated washing. The number of times of washing using an aqueous solution of the base depends on the types of the acid component constituting the active ester, the coexisting condensed peptide compound (an intermediate) and the aqueous solution of the base to be used for washing. Therefore, it is difficult to uniformly specify the number of times of washing; however, it is generally preferable to wash twice or more, more preferably three times or more, and further more preferably four times or more. The number of times of washing can be appropriately set by considering the balance between the decomposition ratio of the active ester and the operation time.

The above-mentioned base to be used for the decomposition of the active ester is not particularly limited, and an inorganic base such as a hydroxide salt, a carbonate or a bicarbonate of an alkali metal or an alkaline earth metal can be used. Among them, an inorganic base of an alkali metal salt is preferred, and particularly a hydroxide, a carbonate or a bicarbonate of sodium is preferred. These bases may be directly applied in the form of a powder, or may be added in the form of an aqueous solution or an aqueous suspension. It is generally preferred that the bases are handled as an aqueous solution having an appropriate concentration. When a reaction solvent containing water is used in Step A, the base in the form of a powder can be added to the reaction system to form an alkaline aqueous solution in the system.

The method of confirming the amount of the remaining active ester is not particularly limited. For example, the reaction mixture, i.e. organic layer, is appropriately sampled, and the amount of the remaining active ester relative to the condensed peptide compound is confirmed by an HPLC analysis or the like, and the endpoint of the decomposition reaction of the active ester may be determined.

The reaction mixture obtained in the above-mentioned Step A may be directly brought into contact with the base; or if necessary, the reaction mixture may be directly brought into contact with the base, after the reaction mixture of Step A is condensed or subjected to solvent replacement, or after a solvent is added to the reaction mixture of Step A. Further, if necessary, the reaction mixture may be brought into contact with the base, after an insoluble substance is removed by filtration or the like. When the solvent is replaced or a fresh solvent is added, the solvent to be used for replacement or to be added is not particularly limited as long as the solvent is essentially inert to the condensed product, and any of the reaction solvents illustrated in the description of the above-mentioned Step A can be used.

The temperature of this reaction is not particularly limited as long as the temperature is not lower than the solidification temperature of the reaction mixture and not higher than the boiling point of the reaction mixture. However, there is a general tendency that an unfavorable side reaction is increased as the reaction temperature is higher. Therefore, the reaction temperature is preferably 40° C. or lower, and more preferably 30° C. or lower. In general, this reaction is preferably carried out at about 0 to 30° C.

The concentration of the reaction mixture is not particularly limited as long as the respective components are dissolved in either the organic layer or the aqueous layer, or at least in a homogenously dispersed state therein. The reaction concentration cannot be uniformly specified, since the reaction concentration is affected by the types of the solvent and the above-mentioned respective components as solutes, the used amount thereof, the reaction temperature and the like. However, this reaction can be generally carried out under a condition that the organic solvent in an amount of 4 to 50 times volume relative to the weight of the condensed product is used. The condition corresponds to a condition that the condensed product concentration in the organic layer is about 2 to 25 w/v %.

It is preferred that the amount of the remaining active ester in the reaction mixture obtained by this reaction, i.e. the reaction mixture after the hydrolysis treatment, is reduced to generally 1% or less, preferably 0.5% or less, and more preferably 0.1% or less, relative to the reaction mixture. It is possible to suppress the by-production of an impurity peptide in the subsequent deprotection reaction and to elongate a peptide chain with high purity and in good yield, by reducing the acid component active ester in this step.

The above-mentioned reaction mixture contains the acid component which is a decomposed product of the acid component active ester and an impurity derived from the activating substituent and also the condensing agent and an impurity derived from the condensing agent in a large number. For example, when EDC is used as a water-soluble carbodiimide and an OBt ester is prepared by dehydration-condensation of the acid component and HOBt, the acid component and HOBt and also EDC and EDUrea are contained in the reaction mixture as impurities. Accordingly, it is preferred that these impurities should also be removed in addition to the above-mentioned decomposition procedure for the acid component active ester.

The method of removing these impurities is not particularly limited, and a common separation-purification method such as extraction or crystallization can be used. It is generally preferred that extraction and washing for removing water-soluble impurities are carried out by retaining the condensed product in the organic layer and washing with a basic aqueous solution and an acidic aqueous solution, and if necessary with water sequentially.

Subsequently, an extraction and washing procedure is described.

The reaction mixture of the above-mentioned Step A and the reaction mixture obtained by decomposing the acid component active ester may be directly subjected to extraction and washing; or if necessary, the reaction mixture may be subjected to extraction and washing, after the reaction mixture is condensed, or a fresh solvent is added thereto, or the solvent is replaced with another solvent. Further, if necessary, the reaction mixture may be subjected to extraction and washing after an insoluble substance is removed by filtration or the like. In the case where the solvent is replaced or a fresh solvent is added, the solvent to be used for replacement or to be added is not particularly limited as long as the solvent is essentially inert to the condensed product, and any of the reaction solvents illustrated in the description of the above-mentioned Step A can be used.

When the solvent in the reaction mixture obtained by the above-mentioned Step A or the decomposition of the acid component active ester is an aprotic polar solvent miscible with water, the yield of the peptide is decreased in some cases, since the solvent is accompanied by the peptide compound and a part of the peptide compound is transferred to the aqueous layer at the time of removing the impurity from the solvent layer by aqueous washing due to a very high water solubility of the solvent. In this case, it is particularly preferred to improve the extraction ratio by using the aprotic polar solvent miscible with water in combination with a solvent which has a relatively favorable solubility for the peptide compound such as aromatic hydrocarbons, halogenated hydrocarbons, ethers or fatty acid esters.

As the basic aqueous solution to be used in the extraction and washing, any basic aqueous solution containing a common basic compound can be used without being particularly limited. The basic compound is not particularly limited, and examples of the basic compound include the same bases to be used in the step of decomposing the acid component active ester. It is a matter of course that washing with the basic aqueous solution of this step can also be achieved only by separating off the aqueous layer (aqueous solution) from the reaction mixture, when hydrolysis is effected by adding the aqueous solution of the base in the step of decomposing the acid component active ester.

As the acidic aqueous solution to be used in the extraction and washing, any acidic aqueous solution containing a common acidic compound can be used without being particularly limited. The acidic compound is not particularly limited, and an inorganic acid salt such as an alkali metal hydrogen sulfate and dihydrogen phosphate, a mineral acid such as hydrochloric acid and sulfuric acid, or an organic acid such as citric acid can be used. Among them, an acid salt such as potassium hydrogen sulfate and potassium dihydrogen phosphate is preferred.

In the extraction and washing with the use of the above-mentioned basic or acidic aqueous solution, a treatment which is carried out in a common extraction procedure, for example, addition of an inorganic salt such as sodium chloride and sodium sulfate, may be performed in order to facilitate the separation into two layers of the organic layer and the aqueous layer.

The temperature of extraction and washing is not particularly limited as long as the temperature is not lower than the solidification temperature of the reaction mixture and not higher than the boiling point of the reaction mixture. However, there is a general tendency that an unfavorable side reaction is increased, as the temperature is higher. Therefore, the temperature is preferably 40° C. or lower, and more preferably 30° C. or lower. In general, the extraction and washing are preferably carried out at about 0 to 30° C.

The concentration of the reaction mixture extraction and washing is not particularly limited as long as the respective components are dissolved in either the organic layer or the aqueous layer or at least in a homogenously dispersed state therein. The concentration at the time of extraction and washing cannot be uniformly specified, since the concentration is affected by the types of the solvent and the respective components as solutes, the used amount thereof, the reaction temperature and the like. In general, the extraction and washing can be carried out under a condition that the organic solvent in an amount of 4 to 50 times volume relative the weight of the condensed product is used. The condition corresponds to a condition that the condensed product concentration in the organic layer subjected to extraction and washing is about 2 to 25 w/v %.

Among the above-mentioned impurities, the acid component which is a decomposed product of the acid component active ester cannot be fully removed in some cases depending on the types of the amino acid side chain, the functional group or the protecting group for such a group. In this case, for example, the organic layer after removing basic impurities such as EDC and EDUrea by the above-mentioned extraction and washing procedure may be subjected to crystallization described below.

Hereinafter, a method of purification by crystallizing the condensed peptide compound is described. As a good solvent in the crystallization of the peptide compound, halogenated hydrocarbons, fatty acid esters or aprotic polar solvents, which have a relatively favorable solubility for the peptide compound, is preferably used among the reaction solvents to be used in the above-mentioned Step A. As the halogenated hydrocarbons, dichloromethane and chlorobenzene are particularly preferred. As the fatty acid esters, ethyl acetate is particularly preferred. As the aprotic polar solvents, DBF, DMF and DMSO are particularly preferred, and above all, DBF which is an aprotic polar solvent immiscible with water is particularly preferred. As the good solvent, particularly preferred are dichloromethane, DBF, DMF and DMSO.

Above all, DBF which is an aprotic polar solvent immiscible with water is preferred. These solvents may be used alone or by mixing two or more kinds.

In order to crystallize the peptide compound, the solubility of the peptide compound is decreased by directly adding an appropriate poor solvent to the solution of a good solvent or of a mixed solvent containing a good solvent, or adding the poor solvent while or after distilling off an unnecessary solvent by condensation, thereby to deposit the peptide compound. Further, so-called reaction crystallization in which Step A and Step B are carried out in a mixed solvent of a good solvent and a poor solvent and the produced condensed product is sequentially deposited can also be favorably performed.

The poor solvent is not particularly limited as long as the poor solvent is a solvent which has a lower solubility for the peptide compound than the good solvent and is essentially inert to the peptide compound. Examples of the poor solvent may include aliphatic hydrocarbons such as hexane and heptane; aromatic hydrocarbons such as toluene and xylene; halogenated hydrocarbons such as dichloromethane, chloroform, 1,2-dichloroethane and chlorobenzene; ethers such as tetrahydrofurane, 1,4-dioxane, t-butylmethyl ether and diisopropyl ether; and fatty acid esters such as methyl acetate, ethyl acetate and isopropyl acetate. Among them, halogenated hydrocarbons, aromatic hydrocarbons, ethers and fatty acid esters, which have a relatively high solubility for the respective reagents to be commonly used in a liquid phase peptide synthesis method, such as the acid component, the activating reagent, the condensing agent and the deprotecting reagent, are preferably used.

As the halogenated hydrocarbons, chlorobenzene is particularly preferred. As the aromatic hydrocarbons, toluene is particularly preferred. As the ethers, t-butylmethyl ether and diisopropyl ether are particularly preferred. As the fatty acid esters, ethyl acetate is particularly preferred. Further, it is also preferred that water is used as the poor solvent. For example, it does not matter that the basic or acidic aqueous solution used for washing away the impurity in the above-mentioned washing step is directly used as the poor solvent. These poor solvents may be used alone or by mixing two or more kinds.

The used amount of the good solvent is not particularly limited; however, the used amount of the good solvent is generally preferable as small as possible from the viewpoint of improvement of the yield of the peptide compound. The used amount of the good solvent cannot be uniformly specified; however, the crystallization can be generally carried out under a condition that the total used amount of the organic solvent relative to the number of moles of the peptide compound is about 0.1 to 10 times volume (L/mol). The used amount can be set to preferably 5 times volume or less, and more preferably 2 times volume or less.

The used amount of the poor solvent is not particularly limited as long as the amount falls within the range in which the fluidity of the crystallization liquid can be maintained and the crystallization yield can be ensured. The used amount of the poor solvent cannot be uniformly specified, since the used amount is affected by the type of the peptide compound, the used amount of the good solvent, the crystallization temperature and the like. However, the crystallization can be generally carried out under a condition that the total used amount of the poor solvent relative to the number of moles of the peptide compound is about 4 to 50 times volume. The condition corresponds to a condition that the condensed product concentration is about 0.02 to 0.25 mol/L.

The temperature at the time of crystallization is not particularly limited; however, it is preferred to allow the crystallization to proceed slowly in order to form a crystallization liquid (slurry) having a favorable property. It is a matter of course that so-called cooling crystallization in which crystallization is allowed to proceed slowly by gradually cooling a reaction system can also be preferably carried out. Further, it is also preferred to add a seed crystal to the reaction system in order to allow the crystallization to proceed smoothly.

With regard to the acid component which cannot be fully removed even by the above-mentioned washing or crystallization, a removal method in Step D after the acid component is deprotected in Step C described below can also be favorably carried out.

Subsequently, Step C is described. Step C is a step of removing the protecting group for the N-terminal amino group of the condensed product obtained in Step B. The obtained condensed product of which the N-terminal amino group is deprotected becomes the amine component for an additional condensation reaction (an elongation reaction) in the middle stage of the peptide chain elongation.

The method of removing the protecting group for the N-terminal amino group is not particularly limited as long as the protecting groups (semipermanent protecting groups) for the C-terminal carboxyl group and the side chain functional group are stable. As the method, known deprotection methods described in, for example, "Pepuchido Gosei no Kiso to Jikken" (Basic Concepts and Experiments of Peptide Synthesis), Maruzen Co. Ltd. (1985), "Protective Groups in Organic Synthesis, the third edition", John Willy & Sons Inc., (1999) and the like can be employed. Examples of the protecting group may include an urethane-type protecting group, an acyl-type protecting group and an sulfonyl-type protecting group; and examples of the deprotection method may include a deprotection method carried out under an acidic condition, a deprotection method carried out under a catalytic reduction condition and a deprotection method carried out under a basic condition. The deprotection method can be selected depending on the protecting group. Hereinafter, a typical method of removing the protecting group for the N-terminal amino group will be illustrated.

First, a method of removing a Boc group is described. The Boc group is a protecting group for the amino group, which can be removed under a relatively mild acidic condition. In order to obtain a reaction system under the acidic condition, an acidic substance may be added to the reaction system as a deprotecting reagent. The acidic substance to be added is not particularly limited; however, halogenated hydrogens such as hydrogen fluoride, hydrogen chloride and hydrogen bromide, mineral acids such as sulfuric acid and nitric acid, carboxylic acids such as formic acid, acetic acid and trifluoroacetic acid (TFA), sulfonic acids such as methanesulfonic acid and p-toluenesulfonic acid, and a mixture thereof can be used. Examples of the mixture may include hydrogen bromide/acetic acid, hydrogen chloride/dioxane and hydrogen chloride/acetic acid. Among them, when an acid which is not an aqueous solution, for example, formic acid, methanesulfonic acid or the like is used in a non-aqueous system, it is also possible to selectively remove the Boc group while, for example, an ester-type protecting group for the carboxyl group which is subject to hydrolysis under an acidic condition is left intact. Above all, sulfonic acids which are soluble in water and in a liquid form at room temperature, such as methanesulfonic acid, are particularly preferred, since the sulfonic acids can allow the reaction to promptly proceed with a relatively small used amount under room temperature and can be easily removed into an aqueous layer after completion of the reaction in the case of being used in a non-aqueous system.

Subsequently, a method of removing a Z group is described. The Z group is a protecting group for the amino group, which can be removed under a relatively mild catalytic reduction condition. In order to obtain a reaction system under the catalytic reduction condition, a catalyst and a hydrogen donor may be added to the reaction system as deprotecting reagents. The catalyst is not particularly limited; however, palladium-black, 5 to 10% palladium-carbon, 5 to 10% palladium hydroxide-carbon or the like can be used. The hydrogen donor is not particularly limited; however, hydrogen gas, a formic acid compound or the like is generally used.

Finally, a method of removing an Fmoc group is described. The Fmoc group is a protecting group for the amino group, which can be removed under a relatively mild basic condition. In order to obtain a reaction system under the basic condition, a basic substance may be added to the reaction system as a deprotecting reagent. The basic substance to be added is not particularly limited; however, secondary amines such as diethylamine, piperidine and morpholine, tertiary amines such as diisopropylethylamine and p-dimethylaminopyridine, and the like are preferably used.

The reaction solvent to be used in this step is not particularly limited as long as the solvent is a solvent which is essentially inert to the condensed product, the amine component, and the respective reagents to be used in this step, such as a deprotecting reagent. Examples of the reaction solvent may include the same reaction solvents as described in Step A. It is a matter of course that the reaction solvent used in the above-mentioned Step B may be directly used, or a fresh solvent is added thereto, or the solvent may be replaced with another solvent.

The reaction temperature of this step is not particularly limited as long as the temperature is not lower than the solidification temperature of the reaction mixture and not higher than the boiling point of the reaction mixture. There is a general tendency that an unfavorable side reaction is increased, as the reaction temperature is higher. Therefore, the reaction temperature is preferably 40° C. or lower, and more preferably 30° C. or lower. In general, this step is preferably carried out at about 0 to 30° C.

The reaction concentration for this step is not particularly limited as long as the respective components are dissolved or at least in a homogenously dispersed state. The reaction concentration cannot be uniformly specified, since the reaction concentration depends on the types of the solvent and the respective components as solutes, the used amount thereof, the reaction temperature and the like. However, this step can be generally carried out under a condition that the total used amount of the organic solvent relative to the weight of the condensed product is about 4 to 50 times volume. The condition corresponds to a condition that the condensed product concentration is about 2 to 25 w/v %.

In this step, the deprotection reaction can proceed quantitatively. The reaction conversion ratio in this step can be expected to be at least 99% or more, generally 99.5% or more, preferably 99.9% or more.

After the deprotection reaction, the condensed product deprotected at the N-terminal amino group can be purified by removing an impurity from the reaction mixture if necessary. The purified condensed product is subjected to an additional condensation reaction (an elongation reaction) as the amine component in the middle stage of the peptide chain elongation. Hereinafter, this purification step is referred to as Step D, and the details are described below.

In the reaction mixture obtained in Step C, a by-product derived from the removed protecting group for the N-terminal amino group and the deprotecting reagent are contained as impurities.

Further, when the excess acid component could not be fully removed in the above-mentioned Step B, the deprotected compound of the acid component, that is, an amino acid derivative or a peptide in which both of the N-terminal amino group and the C-terminal carboxyl group are unprotected and which is derived from the acid component, is also contained in the reaction mixture as one of the impurities. This deprotected compound of the acid component can behave as the acid component or the amine component in an additional elongation reaction, i.e. Step A (a condensation reaction) of the subsequent cycle, and can cause the by-production of various impurity peptides; therefore, these impurities are preferably removed by carrying out this step.

The method of removing these impurities is not particularly limited, and a common separation and purification method such as extraction or crystallization can be used. It is generally preferred that extraction and washing for removing water-soluble impurities are carried out by retaining the condensed product in the organic layer and washing the organic layer with a basic and/or acidic aqueous solution.

The reaction mixture obtained in Step C may be directly subjected to extraction and washing, or if necessary, the reaction mixture may be subjected to extraction and washing after the reaction mixture is condensed or subjected to solvent replacement, or after a solvent is added to the reaction mixture. Further, if necessary, the reaction mixture may be subjected to extraction and washing after an insoluble substance is removed by filtration or the like. As the solvent to be used for the solvent replacement or solvent addition, a similar solvent to those used in the case of extraction and washing in the above-mentioned Step B can be used. As described above, it is particularly preferable to use the aprotic polar solvent miscible with water in combination with another solvent in a similar manner to in Step B, since the aprotic polar solvent miscible with water has a very high water solubility.

Further, the condensed product deprotected at the N-terminal amino group or a salt of the condensed product with an acid may be crystallized for purification from the organic layer after washing with the aqueous solution. As the good solvent to be used in this embodiment, the same good solvents as those used in the purification method by crystallization in Step B can be used. In order to crystallize the peptide compound, the peptide compound is deposited directly by adding an appropriate poor solvent thereto, or while or after distilling off an unnecessary solvent by condensation to decrease the solubility of the peptide compound. Further, so-called neutralization crystallization, in which a base is added thereto to neutralize the salt of the peptide compound and the acid in a mixed solvent of the good solvent and the poor solvent and the produced peptide compound is sequentially deposited, can also be favorably carried out.

As the condition for crystallization, such as the type of the poor solvent to be used, the used amount of the solvent and the temperature, the same condition described in the purification method by crystallization in Step B can be used.

On the other hand, purification in this step is not necessarily required, since the impurity other than the remaining acid component do not adversely affect Step A (a condensation reaction) of the subsequent cycle in most cases. For example, when the purified condensed product of which the protecting group for the N-terminal amino group is a Boc group and from which the excess acid component is fully removed in the above-mentioned Step B is deprotected using methanesulfonic acid as the deprotecting reagent, isobutylene, carbon dioxide gas and methanesulfonic acid are contained as impurities in the reaction mixture. Both of the isobutylene and carbon dioxide gas can be easily removed, since both of them does not adversely affect the subsequent Step A (the condensation reaction) and are in a gaseous form at room temperature. Methanesulfonic acid adversely affects Step A, since methanesulfonic acid can mask the nucleophilicity of the amino group which is a reaction site of the amine component in the condensation reaction. However, methanesulfonic acid can be made harmless by, for example, neutralizing methanesulfonic acid with a base such as a tertiary amine which does not adversely affect the condensation reaction, for example triethylamine. Therefore, it is also possible to omit the removal of the impurity by this step.

The condition such as the temperature of extraction and washing and the concentration of the condensed product is the same as the condition for the extraction and washing described in Step B.

As described above, in the first invention of the present application, the target peptide having high purity can be obtained by suppressing the by-production of the impurity peptide derived from the acid component active ester and accumulation thereof, even when the above-mentioned Steps A, B, C and D are sequentially and continuously performed, since the unreacted acid component active ester is decomposed until the amount of the remaining active ester is decreased to 1% or less in Step B. Accordingly, the effect of the present invention is maximally exerted, when a peptide consisting of 3 or more amino acid residues, preferably 4 or more amino acid residues, particularly preferably 5 or more amino acid residues is synthesized.

The first invention of the present application is not necessarily required to start from Step A and finish at Step C or Step D. Further, the Steps A, B and C may be respectively carried out at least once, and it is not necessarily required to carry out all of Steps A, B and C in the same number of times. Step D may be carried out if necessary and is not an essential step in the first invention of the present application. The first invention can start from any step according to an available raw material. For example, the first invention can start from Step C when the amino acid or the peptide of which the N-terminal amino group is protected can be easily obtained. Further, the first invention can finish at any step according to the target peptide compound. For example, a peptide of which the N-terminal amino group is protected and which is obtained by the steps up to Step B is subjected to a deprotection reaction of the side chain functional group through a known method.

Subsequently, the method of producing a peptide which is a second invention of the present application is described. A second invention of the present application is a method of producing a peptide by a liquid phase synthesis method, comprising steps of:

Step A: a step of reacting an active ester of an acid component with an amine component to obtain a condensed compound;

Step B: a step of purifying the condensed compound by removing an impurity in a reaction mixture obtained in Step A;

Step C: a step of removing a protecting group for an N-terminal amino group of the condensed compound obtained in Step B; and Step D: a step of purifying the condensed compound deprotected at the N-terminal amino group by removing an impurity in a reaction mixture obtained in Step C, if necessary;

wherein, an amide-type solvent immiscible with water is used in at least one of the steps.

In the case where the liquid phase peptide synthesis is carried out by using, for example, DMF which is an amide-type solvent miscible with water as the reaction solvent, as described above, the solvent is accompanied by the peptide compound and a part of the peptide compound is transferred to the aqueous layer and thus the yield of the peptide is decreased in some cases in the extraction and washing of Step B at the time of removing an unnecessary reagent from the solvent layer by aqueous washing. In such a case, the extraction ratio can be intended to be improved by, for example, removing DMF having a high boiling point for condensation or by using a large amount of an extraction solvent; however, complication of the operation or an increase in the amount of the extraction solvent is caused. Further, even if the treatment as described above is carried out, DMF is not sufficiently retained in the solvent layer and partitioned into the aqueous layer; as a result, a large amount of the peptide is deposited from the solvent layer and liquid separation cannot be carried out in some cases.

On the other hand, in the case where the liquid phase peptide synthesis is carried out using the amide-type solvent immiscible with water as the reaction solvent, the liquid separation operation can be performed while maintaining the solubility of the peptide, since the amide-type solvent immiscible with water is retained in the solvent layer.

Further, there is a tendency that the reaction rate of the condensation reaction is decreased as the peptide chain is elongated in the liquid phase peptide synthesis; however, it was found that the reaction rate of the condensation reaction is increased and the reaction can be promptly completed by using the amide-type solvent immiscible with water as the reaction solvent.

As described above, it was found that the amide-type solvent immiscible with water has an ideal property for the overall liquid phase synthesis method, particularly the continuous liquid phase synthesis method. In the second invention of the present application, the amide-type solvent immiscible with water is used in at least one step of the above-mentioned Steps A to D on the basis of this finding. Specifically, the above-mentioned phrase means that at least one of the following a) to d) is included:

a) a solvent containing the amide-type solvent immiscible with water is used as the reaction solvent in the condensation reaction of Step A;

b) a solvent containing the amide-type solvent immiscible with water is used as the solvent of the organic solvent layer containing the condensed product, which is subjected to purification such as decomposition, extraction and washing, and/or crystallization of the acid component active ester in Step B;

c) a solvent containing the amide-type solvent immiscible with water is used as the reaction solvent when the protecting group for the N-terminal amino group of the condensed product is removed in Step C; and d) a solvent containing the amide-type solvent immiscible with water is used as the solvent of the organic solvent layer containing the condensed product subjected to purification such as extraction and washing and/or crystallization in Step D.

It is needless to say that a solvent containing the amide-type solvent immiscible with water can be used in a plurality of steps and purification procedures. When a plurality of purification methods are carried out in Step B or D, it is preferred that a solvent containing the amide-type solvent immiscible with water is used in all the purification procedures from the viewpoint of simplifying the procedures and maximizing the effect of the present invention. For the same reason, it is preferred that a solvent containing the amide-type solvent immiscible with water is used in all Steps A to D.

When the target peptide compound is produced by repeating the cycle of Steps A to D several times, a solvent containing the amide-type solvent immiscible with water may be used from the first cycle, or the solvent containing the amide-type solvent may be used from the middle stage.

The amide-type solvent immiscible with water according to the present invention represent an amide compound which has a structure obtained by dehydration-condensation of a carboxylic acid and a dialkylamine and which is in a liquid form at room temperature and is immiscible with water. Among the reaction solvents illustrated in the first invention of the present application, the amide-type solvent immiscible with water is included in the aprotic polar solvent immiscible with water. The amide-type solvent immiscible with water has the amide bond as the peptide compound; therefore, the amide-type solvent immiscible with water has a very high affinity for the peptide compound and has a high solubility for the peptide. Examples of the amide-type solvent immiscible with water include formamide compounds such as N,N-dipropylformamide and N,N-dibutylformamide (DBF), and acetamide compounds such as N,N-dipropylacetamide and N,N-dibutylacetamide. Among these amide compounds, amide compounds having 7 or more carbon atoms are preferred. Above all, DBF is particularly preferably used, since DBF is excellent in peptide solubility and liquid separation property, and also is easily obtained.

The amide-type solvent immiscible with water may be used alone or by mixing two or more kinds as the reaction solvent or the extraction solvent. Further, the amide-type solvent immiscible with water can also be preferably added to an another common organic solvent, for example, aliphatic hydrocarbons such as hexane and heptane; aromatic hydrocarbons such as toluene and xylene; halogenated hydrocarbons such as dichloromethane, chloroform, 1,2-dichloroethane and chlorobenzene; ethers such as tetrahydrofurane, 1,4-dioxane, t-butylmethyl ether and diisopropyl ether; fatty acid esters such as methyl acetate, ethyl acetate and isopropyl acetate; and the like. Above all, it is also preferable to add the amide-type solvent into an organic solvent such as halogenated hydrocarbons or fatty acid esters, which have a relatively favorable solubility for the respective reagents to be used in the liquid phase peptide synthesis and the peptide compound. As the halogenated hydrocarbons, dichloromethane and chlorobenzene are particularly preferred, and as the fatty acid ester, ethyl acetate is particularly preferred.

The used amount of the amide-type solvent immiscible with water is not particularly limited as long as the respective reagents to be used in the liquid phase peptide synthesis are dissolved in either the organic layer or the aqueous layer or at least in a homogenously dispersed state therein. However, in general, the used amount of the amide-type solvent immiscible with water is preferably as large as possible from the viewpoint of the peptide solubility. The used amount of the amide-type solvent immiscible with water cannot be uniformly specified, since the used amount is affected by the types of the respective reagents as solutes and are used in the liquid phase peptide synthesis, other organic solvents to be used by mixing, the used amount thereof, the reaction temperature and the like. However, in general, the total used volume (L/mol) of the amide-type solvent immiscible with water relative to the sum of the number of moles of the above-mentioned amine component, the condensed product and the condensed product deprotected at the N-terminal amino group is 0.1 times volume or more, more preferably 1 times volume or more, and particularly preferably 2 times volume or more. The upper limit thereof is 50 times volume or less, more preferably 20 times volume or less, and particularly preferably 10 times volume or less.

The amide-type solvent immiscible with water has an extremely high solubility, and the peptide can be dissolved and the liquid property can be improved by adding only an extremely small amount of the amide-type solvent immiscible with water; therefore, it is preferred that the used amount of the amide-type solvent immiscible with water is decreased as low as possible from the viewpoint of the productivity, and a required minimum used amount of the amide-type solvent may be set while the dissolved state is confirmed. The used amount can be set to preferably 10 times volume or less, more preferably 5 times volume or less, and particularly preferably 2 times volume or less. It is a matter of course that the amide-type solvent immiscible with water can also be preferably added for the purpose of eliminating the problem, for example, for dissolving the deposited peptide compound, when a problem such as deposition of the peptide compound is confirmed in the extraction and washing step of Step B in the first invention of the present application.

In the liquid phase peptide synthesis using the amide-type solvent immiscible with water, the concentrations of the above-mentioned amine component, condensed product, and fresh amine component in the organic solvent layer cannot be uniformly specified, since such concentrations are affected by the types of the respective reagents to be used, the used amount thereof, the composition of the organic solvent, i.e. a solvent mixing ratio, the reaction temperature and the like. However, the reaction can be generally carried out under a condition that the total used volume (L/mol) of the organic solvent relative to the sum of the number of moles of the above-mentioned amine component, condensed product and fresh amine component is about 1 to 50 times volume. The total used volume thereof can be set to more preferably 20 times volume or less, and further more preferably 10 times volume or less.

In the liquid phase synthesis method of a peptide compound characterized by using the amide-type solvent immiscible with water, the detailed methods of the above-mentioned Steps A, C and D are the same as described in the first invention except that the above-mentioned solvent is used as the solvent.

The detailed method of the above-mentioned Step B is not particularly limited, and the above-mentioned decomposition step, extraction and washing step and crystallization step of the active ester may be carried out, or known methods such as the method by Carpino et al. (Org. Proc. Res. Dev., 7, 28 (2003), U.S. Pat. No. 5,516,891) or the DioRaSSP method by Diosynth (JP-A-2003-55396) in which the acid component active ester is decomposed using a scavenger can be used without limitation.

It is needless to say that the first invention of the present application in which the unreacted acid component active ester is hydrolyzed while maintaining the reaction system in a basic condition until the amount of the remaining unreacted acid component active ester is decreased to 1% or less in Step B may be carried out also in the second invention. In Step B of the second invention of the present application, the amount of the remaining unreacted acid component active ester is not particularly limited; however, it is more preferred that the remaining amount thereof is decreased to 1% or less from the same reason described in the first invention of the present application.

The amide-type solvent preferably works in the purification of the peptide compound, since the amide-type solvent has a selective interaction with the peptide compound in a peptide mixture containing various impurities due to a high affinity for the peptide compound. As the method of purifying the peptide compound contained in the organic solvent solution including the amide-type solvent immiscible with water, purification methods by the washing method and the crystallization method in the above-mentioned Step B or Step D can be preferably carried out. Further, when the amide-type solvent immiscible with water is used as the good solvent in the crystallization method, the impurity can be more effectively removed. Furthermore, it is preferable in Step D to remove the impurity by crystallization using the amide-type solvent immiscible with water in the presence of an acid and to purify the salt of the acid with the peptide compound in which the N-terminal amino group is unprotected and the C-terminal carboxyl group is protected, since the peptide compound of higher purity can be obtained.

The method of purifying the salt of the acid with the peptide compound in which the N-terminal amino group is unprotected and the C-terminal carboxyl group is protected by depositing the contaminating impurity by carrying out crystallization using the amide-type solvent immiscible with water and removing the deposited impurity in the above-mentioned Step D is described. In this purification method, the impurity is separated off while retaining the salt of the peptide compound with the acid in the organic solvent layer by utilizing the fact that the salt of the peptide compound with the acid has a high affinity for the amide-type solvent immiscible with water. For example, in the case such that the hydrophilicity of the acid component which is a decomposed product of the active ester is low, the acid component cannot be fully removed in Step B in some cases. In such a case, the acid component is converted to a deprotected product of the acid component by the subsequent deprotection reaction, and the salt of the deprotected product of the acid component obtained by adding an acid after the deprotection has a low affinity for the amide-type solvent immiscible with water; therefore, the salt of the deprotected product of the acid component can be easily removed, since the salt is separated out as a solid from the organic solvent. In this manner, the salt of the peptide compound with the acid can be efficiently purified. When the deprotection in Step C is carried out under an acidic condition, it is not necessarily to add the acid. In the case where the peptide compound does not form the salt with the acid, the peptide compound may be converted to the salt with an acid by suitably adding the acid. As the acid to be added in this case, a commonly used inorganic acid or organic acid may be used.

The used amount of the amide-type solvent immiscible with water is not particularly limited. In general, the used amount is preferably as small as possible from the viewpoint of improvement of the removal ratio of the salt of the acid component deprotected product with the acid. The used amount of the amide-type solvent immiscible with water cannot be uniformly specified; however, this procedure can be generally carried out under a condition that the total used volume (L/mol) of the organic solvent relative to the number of moles of the peptide compound is about 0.1 to 10 times volume. The total used volume thereof can be set to preferably 5 times volume or less, and more preferably 2 times volume or less.

The amide-type solvent immiscible with water may be used as an organic solvent mixture with another solvent. Examples of such another solvent may include the same solvents as illustrated in the reaction solvent used in Step A. Among them, halogenated hydrocarbons and fatty acid esters, which have a relatively favorable solubility for the peptide compound is preferably used. As the halogenated hydrocarbons, dichloromethane and chlorobenzene are particularly preferred. As the fatty acid esters, ethyl acetate is particularly preferred. Particularly preferred are dichloromethane and chlorobenzene.

The used amount of such another solvent is not particularly limited as long as the used amount falls within the range in which the fluidity of the reaction mixture having the salt of the acid component deprotected product with the acid deposited therein can be maintained and the dissolved amount of the salt of the peptide compound with the acid is not saturated. The used amount of another solvent cannot be uniformly specified, since the used amount is affected by the type of the above-mentioned peptide compound, the used amount of the amide-type solvent immiscible with water, the crystallization temperature and the like. This procedure can be generally carried out under a condition that the total used amount of the solvent relative to the number of moles of the above-mentioned peptide compound is about 4 to 100 times volume. The condition corresponds to a condition that the fresh amine component concentration is about 0.01 to 0.25 mol/L.

The temperature at the time of the above-mentioned crystallization is not particularly limited; however, it is preferred to allow the crystallization to proceed slowly in order to form a crystallization liquid (slurry) having a favorable property. It is a matter of course that so-called cooling crystallization in which crystallization is allowed to proceed slowly by gradually cooling the reaction system can also be carried out. Further, it is also preferred to add a seed crystal to the reaction system in order to allow the crystallization to proceed smoothly.

In the purification method, the salt of the peptide compound with the acid is obtained as a solution containing the peptide-type solvent immiscible with water; however, the salt is subsequently neutralized when washing with a basic aqueous solution is carried out in the extraction and washing step of Step D and can be converted to a free peptide compound, in a similar manner to the method of the first invention of the present application. The obtained free peptide compound can also be crystallized by being subjected to the crystallization step of Step D like the method of the first invention of the present application.

As another effect exerted by the amide-type solvent immiscible with water, acceleration of the condensation reaction can be exemplified. The effect of acceleration of the condensation reaction cannot be uniformly specified, since the acceleration effect is affected by the combination of the acid component and the amine component to be condensed, the types of the respective reagents such as the activating reagent and the condensing agent, the used amount thereof, the type or composition of the organic solvent (a solvent mixing ratio), the reaction temperature and the like. However, the reaction can generally be completed within 10 hours, preferably within 5 hours, more preferably within 3 hours, due to the acceleration effect. In addition, even a relatively unstable peptide compound can be obtained with high purity and in good yield without decomposition by reducing the reaction time, since the reaction can be completed in a short time.

The liquid phase synthesis method of a peptide compound characterized by using the amide-type solvent immiscible with water as described above can be applied to the overall liquid phase peptide synthesis method without particularly limitation, such as the method of decomposing an active ester.

Further, a peptide compound of high purity can also be more efficiently produced by combining the liquid phase synthesis method using the amide-type solvent immiscible with water with the liquid phase peptide synthesis method of the first invention of the present application.

EXAMPLES

Hereinafter, the present invention is described with reference to Examples; however, the invention is not limited to these Examples.

In the present Examples, abbreviations which are based on the code of the IUPAC-IUB Joint Commission or are conventionally used in the field were used for peptide compounds, protecting groups and the like. Further, in the case where optical isomers exist with regard to amino acids, the L-form is represented unless otherwise specified.

As the abbreviations for reagents, EDC: 1-(3-dimethylaminopropyl)-3-ethylcarbodiimide, and HOBt: 1-hydroxybenzotriazole were used.

As the abbreviations for protecting groups and substituents, Bn: benzyl group, Boc: t-butoxycarbonyl group, Et: ethyl group, OBt: 1H-benzotriazol-1-yloxy group, and Ts: p-toluenesulfonyl group were used.

As the abbreviations for amino acids, Arg(Ts): Ng-p-toluenesulfonylarginine, D-Leu: D-leucine, Gly: glycine, Leu: leucine, Phe: phenylalanine, Pro: proline, Ser(Bn): O-benzylserine, and Tyr(Bn): O-benzyltyrosine were used.

The pH in the following Examples and the like were measured by glass electrode method using a handy pH meter D21S type manufactured by Horiba Instruments Company with 3-point calibration using a phthalate standard solution, a neutral phosphate standard solution and a borate standard solution, which are specified in the pH measurement method of JIS Z 8802.

The purity of a target peptide compound, i.e. a main component, the content of impurity, and the remaining amount of the active ester were measured using HPLC (column: manufactured by YMC Co., Ltd., YMC-Pack ODS-A A303, mobile phase: 10 mM phosphate buffer (pH 2.5)/acetonitrile=60/40 to 20/80, detector: UV 210 nm) equipped with a UV detector). The remaining amount of the active ester was traced by the transition of the content of the active ester in the target peptide compound.

The purity of the main component, the content of the impurity and the content of the active ester were calculated by the following calculation formulae. The total peak area value was calibrated by subtracting the peak area value of a solvent such as chlorobenzene or DBF.

Reaction conversion ratio=area value of target compound/(area value of target compound+area value of raw material)×100(%)

Purity of main component=area value of the main component/total peak area value×100(%)

Content of impurity=area value of impurity/area value of main component×100(%)

Content of active ester=area value of active ester/area value of main component×100(%)

Example 1

Synthesis of Boc-Arg(Ts)-Pro-NHEt

To a solution composed of Boc-Pro-NHEt (2.0 g) and dichloromethane (20 ml), methanesulfonic acid (1.90 g) was added at room temperature, and the resulting mixture was stirred at room temperature for 4 hours, thereby the Boc group was removed (reaction conversion ratio: 100.0%). After the reaction, triethylamine (3 ml) in an amount of the same molar equivalent as that of the added methanesulfonic acid was added thereto, and the resulting mixture was stirred for 15 minutes. After Boc-Arg(Ts) (4.24 g) and HOBt monohydrate (1.67 g) were added to the thus obtained dichloromethane solution of Pro-NHEt, the reaction solution was cooled with ice. Then, EDC hydrochloride (2.37 g) was added thereto, and the resulting mixture was stirred for 1 hour. Subsequently, the temperature of the mixture was raised to room temperature and the mixture was stirred for 15 hours, thereby performing a condensation reaction.

After the reaction, 5% aqueous sodium carbonate solution (20 ml) was added thereto, and the resulting mixture was stirred for 15 minutes. Then, the aqueous layer was separated off. The pH of the aqueous layer at this time was 7.6, and the content of Boc-Arg (Ts)-OBt as the active ester in the obtained organic layer was 0.2% and Boc-Arg(Ts) as the acid component therein was not detected. The pH of the aqueous layer obtained by repeating this procedure one more time was 10.9, and the content of Boc-Arg(Ts)-OBt in the obtained organic layer was 0.04%. The pH of the aqueous layer obtained by further repeating this procedure one more time was 11.8, and Boc-Arg(Ts)-OBt was not detected in the obtained organic layer.

The obtained organic layer was washed once with water (20 ml), and then washed twice with 5% aqueous potassium hydrogen sulfate solution (20 ml). The obtained organic layer was condensed under reduced pressure, thereby a condensed product (4.39 g) was obtained. The purity of the target Boc-Arg (Ts)-Pro-NHEt was 96% and the yield was 94%.

Example 2

Synthesis of Boc-D-Leu-Leu-Arg (Ts)-Pro-NHEt

Boc-Leu-Arg (Ts)-Pro-NHEt was prepared from Boc-Arg (Ts)-Pro-NHEt obtained in Example 1 and Boc-Leu by the same procedure as Example 1. To a solution composed of the compound (0.969 g) and dichloromethane (10 ml), methanesulfonic acid (0.78 g) was added at room temperature, and the resulting mixture was stirred at room temperature for 4 hours, thereby the Boc group was removed (reaction conversion ratio: 100.0%). After the reaction, triethylamine in an amount of the same molar equivalent as that of the added methanesulfonic acid was added thereto, and the resulting mixture was stirred for 15 minutes. After Boc-D-Leu (0.40 g) and HOBt monohydrate (0.33 g) were added to the thus obtained dichloromethane solution of Leu-Arg(Ts)-Pro-NHEt, the reaction solution was cooled with ice. Then, EDC hydrochloride (0.42 g) was added thereto, and the resulting mixture was stirred for 1 hour. Subsequently, the temperature of the mixture was raised to room temperature and the mixture was stirred for 15 hours, thereby performing a condensation reaction (reaction conversion ratio: 100.0%).

After the reaction, 5% aqueous sodium carbonate solution (10 ml) was added thereto, and the resulting mixture was stirred for 15 minutes, and then, the aqueous layer was separated off. The pH of the aqueous layer at the time was 9.3, and the content of Boc-D-Leu-OBt as the active ester in the obtained organic layer was 11.5% and the content of Boc-D-Leu therein was 0.8%. The pH of the aqueous layer obtained by repeating this procedure one more time was 11.0, and the content of Boc-D-Leu-OBt in the obtained organic layer was 0.2% and Boc-D-Leu was not detected. The pH of the aqueous layer obtained by further repeating this procedure one more time was 12.4, and Boc-D-Leu-OBt and Boc-D-Leu were not detected in the obtained organic layer.

The obtained organic layer was washed once with water (10 ml), and then washed twice with 5% aqueous potassium hydrogen sulfate solution (10 ml). The obtained organic layer was condensed under reduced pressure, thereby a condensed product (0.97 g) was obtained. The purity of the target Boc-D-Leu-Leu-Arg(Ts)-Pro-NHEt was 95% and the yield was 85%.

Example 3

Synthesis of Boc-Ser(Bn)-Tyr(Bn)-D-Leu-Leu-Arg (Ts)-Pro-NHEt

Boc-Tyr(Bn)-D-Leu-Leu-Arg(Ts)-Pro-NHEt was prepared from Boc-D-Leu-Leu-Arg(Ts)-Pro-NHEt obtained in Example 2 and Boc-Tyr(Bn) by the same procedure as Example 2. To a solution composed of this compound (0.46 g) and dichloromethane (5 ml), methanesulfonic acid (0.42 g) was added at room temperature, and the resulting mixture was stirred at room temperature for 1 hour, thereby the Boc group was removed (reaction conversion ratio: 99.9%). After the reaction, 5% aqueous sodium carbonate solution (5 ml) was added thereto, and the resulting mixture was stirred for 15 minutes, and then, the aqueous layer was separated off. After Boc-Ser (Bn) (0.19 g) and HOBt monohydrate (0.12 g) were added to the obtained dichloromethane solution of Tyr(Bn)-D-Leu-Leu-Arg(Ts)-Pro-NHEt, the reaction solution was cooled with ice. Then, EDC hydrochloride (0.15 g) was added thereto, and the resulting mixture was stirred for 1 hour. Subsequently, the temperature of the mixture was raised to room temperature and the mixture was stirred for 15 hours, thereby a condensation reaction was carried out (reaction conversion ratio: 99.9%).

After the reaction, 5% aqueous sodium carbonate solution (5 ml) was added thereto, and the resulting mixture was stirred for 15 minutes, and then, the aqueous layer was separated off. The pH of the aqueous layer at the time was 11.1, and the content of Boc-Ser (Bn)-OBt as the active ester in the obtained organic layer was 4.4% and the content of Boc-Ser (Bn) therein was 0.1%. The pH of the aqueous layer obtained by repeating said procedure one more time was 11.3, and the content of Boc-Ser(Bn)-OBt in the obtained organic layer was 2.8% and the content of Boc-Ser(Bn) therein was 1.3%. The pH of the aqueous layer obtained by further repeating said procedure one more time was 11.5, and the content of Boc-Ser(Bn)-OBt in the obtained organic layer was 0.1% and Boc-Ser(Bn) was not detected.

The obtained organic layer was washed once with water (5 ml), and then washed twice with 5% aqueous potassium hydrogen sulfate solution (5 ml). The obtained organic layer was condensed under reduced pressure, thereby a condensed product (0.50 g) was obtained. The purity of the target Boc-Ser (Bn)-Tyr (Bn)-D-Leu-Leu-Arg (Ts)-Pro-NHEt was 83% and the yield was 84%.

Example 4

Synthesis of Boc-Phe-Leu-OBn

To a solution composed of Leu-OBn•TsOH salt (10.02 g), triethylamine (2.58 g) and dichloromethane (100 ml), Boc-Phe (10.13 g) and HOBt monohydrate (7.01 g) were added, and the resulting mixture was cooled with ice. Then, EDC hydrochloride (8.80 g) was added thereto, and the resulting mixture was stirred for 2 hours. Subsequently, the temperature of the mixture was raised to room temperature and the mixture was stirred for 13 hours, thereby a condensation reaction was carried out (reaction conversion ratio: 100.0%).

The pH of the aqueous layer obtained by carrying out with 5% aqueous sodium carbonate solution (100 ml) after the reaction was 8.3, and the content of Boc-Phe-OBt as the active ester in the obtained organic layer was 1.6% and the content of Boc-Phe as the acid component therein was 5.0%. The pH of the aqueous layer obtained by further washing this organic layer with 5% aqueous sodium carbonate solution (100 ml) was 10.4, and the content of Boc-Phe-OBt (an active ester) in the obtained organic layer was 0.1% and the content of Boc-Phe therein was 0.4%.

The thus obtained organic layer was washed once with water (100 ml), and washed with 5% aqueous potassium hydrogen sulfate solution (100 ml), and then washed with saturated brine (100 ml), thereby an organic layer (135.76 g) was obtained. The purity of the target Boc-Phe-Leu-OBn was 95%.

When the organic layer (135.57 g) was condensed under reduced pressure, and the solvent thereof was replaced from dichloromethane to hexane. As a result, a solid was deposited. After the mixture was allowed to mature by stirring for 1 hour under ice-cooling, the deposited solid was collected by filtration, washed with hexane (100 ml) and dried under vacuum, thereby a white solid (10.16 g) was obtained. The purity of the target Boc-Phe-Leu-OBn was 99% and the yield was 84%.

As a result of HPLC determination using the obtained crystal as a reference standard, the yield of Boc-Phe-Leu-OBn in the above organic layer was 95%.

Example 5

Synthesis of Boc-Gly-Gly-Phe-Leu-OBn (SEQ ID NO: 1)

To the organic layer obtained by the same procedure as Example 4, i.e. the solution composed of Boc-Phe-Leu-OBn (0.55 g) and dichloromethane (5 ml), methanesulfonic acid (0.23 g) was added at room temperature, and the resulting mixture was stirred at room temperature for 2 hours, thereby the Boc group was removed (reaction conversion ratio: 100.0%). After the reaction, 5% aqueous sodium carbonate solution (5 ml) was added thereto, and the resulting mixture was stirred for 15 minutes, and then, the aqueous layer was separated off. After Boc-Gly (0.31 g) and HOBt monohydrate (0.32 g) were added to the thus obtained dichloromethane solution of Phe-Leu-OBn, the reaction solution was cooled with ice. Then, EDC hydrochloride (0.41 g) was added thereto, and the resulting mixture was stirred for 1 hour. Subsequently, the temperature of the mixture was raised to room temperature and the mixture was stirred for 15 hours for a condensation reaction (reaction conversion ratio: 99.7%).

After the reaction, 5% aqueous sodium carbonate solution (5 ml) was added thereto, and the resulting mixture was stirred for 15 minutes, and then, the aqueous layer was separated off. The pH of the aqueous layer at this time was 8, and the content of Boc-Gly-OBt as the active ester in the obtained organic layer was 0.1%. The pH of the aqueous layer obtained by repeating said procedure two more times was 12, and Boc-Gly-OBt was not detected in the obtained organic layer.

The obtained organic layer was washed once with water (5 ml), and then washed twice with 5% aqueous potassium hydrogen sulfate solution (5 ml). The obtained organic layer was condensed under reduced pressure, thereby a condensed product (0.54 g) was obtained. The purity of the target Boc-Gly-Phe-Leu-OBn was 87%, and the yield was 88%.

To the solution composed of the thus obtained Boc-Gly-Phe-Leu-OBn (0.54 g) and dichloromethane (5 ml), methanesulfonic acid (0.26 g) was added at room temperature, and the resulting mixture was stirred at room temperature for 1.5 hours, thereby the Boc group was removed (reaction conversion ratio: 100.0%). After the reaction, 5% aqueous sodium carbonate solution (5 ml) was added thereto, and the resulting mixture was stirred for 15 minutes, and then, the aqueous layer was separated off. After Boc-Gly (0.27 g) and HOBt monohydrate (0.28 g) were added to the thus obtained dichloromethane solution of Gly-Phe-Leu-OBn, the reaction solution was cooled with ice. Then, EDC hydrochloride (0.36 g) was added thereto, and the resulting mixture was stirred for 1 hour. Subsequently, the temperature of the mixture was raised to room temperature and the mixture was stirred for 15 hours for a condensation reaction (reaction conversion ratio: 100.0%).

After the reaction, 5% aqueous sodium carbonate solution (5 ml) was added thereto, and the resulting mixture was stirred for 15 minutes, and then, the aqueous layer was separated off. The pH of the aqueous layer at the time was 8, and the content of Boc-Gly-OBt as the active ester in the obtained organic layer was 0.1%. The pH of the aqueous layer obtained by repeating said procedure two more times was 12, and Boc-Gly-OBt was not detected in the obtained organic layer.

The obtained organic layer was washed once with water (5 ml), and then washed twice with 5% aqueous potassium hydrogen sulfate solution (5 ml). The obtained organic layer was condensed under reduced pressure, thereby a condensed product (0.44 g) was obtained. The purity of the target Boc-Gly-Gly-Phe-Leu-OBn (SEQ ID NO: 1) was 92%, and the yield was 73%.

Example 6

Synthesis of Tyr(Bn)-Gly-Gly-Phe-Leu-OBn (SEQ ID NO: 2)

To the solution composed of Boc-Gly-Gly-Phe-Leu-OBn (SEQ ID NO: 1) (0.97 g) obtained by the same procedure as Example 5 and dichloromethane (15 ml), methanesulfonic acid (0.46 g) was added at room temperature, and the resulting mixture was stirred at room temperature for 2 hours, thereby the Boc group was removed (reaction conversion ratio: 100.0%).

After the reaction, 5% aqueous sodium carbonate solution (15 ml) was added thereto, and the resulting mixture was stirred for 15 minutes. Then, the aqueous layer was separated off. After Boc-Tyr(Bn) (0.93 g) and HOBt monohydrate (0.46 g) were added to the obtained dichloromethane solution of Gly-Gly-Phe-Leu-OBn (SEQ ID NO: 3), the reaction solution was cooled with ice. Then, EDC hydrochloride (0.57 g) was added thereto, and the resulting mixture was stirred for 1 hour. Subsequently, the temperature of the mixture was raised to room temperature and the mixture was stirred for 15 hours for a condensation reaction (reaction conversion ratio: 100.0%).

After the reaction, 5% aqueous sodium carbonate solution (15 ml) was added thereto, and the resulting mixture was stirred for 15 minutes. Then, the mixture was left stand, and the aqueous layer was separated off. The pH of the aqueous layer obtained by repeating said procedure two more times was 12, and Boc-Tyr (Bn)-OBt as the active ester was not detected in the obtained organic layer, but the content of Boc-Tyr (Bn) as the acid component therein was 44%.

The obtained organic layer was washed once with water (15 ml), and then washed twice with 5% aqueous potassium hydrogen sulfate solution (15 ml). The obtained organic layer was condensed under reduced pressure, thereby a condensed product (1.25 g) was obtained. The purity of the target Boc-Tyr (Bn)-Gly-Gly-Phe-Leu-OBn (SEQ ID NO: 4) was 61%, and the content of Boc-Tyr(Bn) therein was 44%.

To the solution composed of the obtained condensed product (1.25 g) containing Boc-Tyr(Bn)-Gly-Gly-Phe-Leu-OBn (SEQ ID NO: 4) and dichloromethane (10 ml), methanesulfonic acid (1.32 g) was added at room temperature, and the resulting mixture was stirred at room temperature for 1 hour, thereby the Boc group was removed (reaction conversion ratio: 100.0%).

After the reaction, triethylamine (1.82 g) was added thereto and the resulting mixture was stirred for 5 minutes. Then, 5% aqueous sodium carbonate solution (10 ml) was added thereto, thereby a white solid was deposited. After the mixture was allowed to mature by leaving the mixture stand for 30 minutes, the deposited solid was collected by filtration and washed with dichloromethane (20 ml). The thus obtained filtrate and the washing liquid were combined, and the resulting mixture was washed 3 times with 5% aqueous sodium carbonate solution (20 ml). After the aqueous layer was separated off, the obtained organic layer was condensed under reduced pressure, thereby a condensed product (0.67 g) was obtained. The purity of the target Tyr(Bn)-Gly-Gly-Phe-Leu-OBn (SEQ ID NO: 2) was 82%, and the yield was 57%. Further, the content of Tyr(Bn) was 8%.

On the other hand, the solid obtained by filtration and washing contained Tyr(Bn) as a main component. The purity of Tyr(Bn) was 87%, and the content of Tyr (Bn)-Gly-Gly-Phe-Leu-OBn (SEQ ID NO: 2) was 14% (yield: 4%).

Example 7

Extraction of Boc-Gly-Gly-Phe-Leu-OBn (SEQ ID NO: 1) with Addition of DBF

When chlorobenzene (0.8 ml) was added to Boc-Gly-Gly-Phe-Leu-OBn (SEQ ID NO: 1) (0.117 g) obtained by the same procedure as Example 5, the compound was not completely dissolved. However, when DBF (0.2 ml) was added thereto, the compound was completely dissolved. To the thus obtained solution, 5% aqueous sodium carbonate solution (0.8 ml) and saturated brine (2.4 ml) were added, and the resulting mixture was mixed by shaking. Thereafter, when the resulting mixture was left stand, the mixture was promptly separated into two clear layers. The organic layer and the aqueous layer were separated. The extraction ratio of Boc-Gly-Gly-Phe-Leu-OBn (SEQ ID NO: 1) into the organic layer was 99%, and the partition ratio of DBF into the aqueous layer was 1.4%.

Comparative Example 1

Extraction of Boc-Gly-Gly-Phe-Leu-OBn (SEQ ID NO: 1) with the Addition of DMF

When chlorobenzene (0.8 ml) was added to Boc-Gly-Gly-Phe-Leu-OBn (SEQ ID NO: 1) (0.117 g) obtained by the same procedure as Example 5, the compound was not completely dissolved therein. However, when DMF (0.2 ml) was added thereto, the compound was completely dissolved. To the thus obtained solution, 5% aqueous sodium carbonate solution (0.8 ml) and saturated brine (2.4 ml) were added, and the resulting mixture was mixed by shaking. Thereafter, when the resulting mixture was left stand, a large amount of crystals were deposited from the organic layer and the organic layer lost the fluidity. The aqueous layer was taken out and analyzed, and as a result, it was found that 100% DMF was partitioned in the aqueous layer.

From the results of Example 6 and Comparative example 1, it was found that the extraction procedure is improved by the amide-type solvent immiscible with water, such as DBF.

Example 8

Synthesis of Boc-Phe-Leu-OBn with chlorobenzene Solvent

To the solution composed of Leu-OBn·TsOH salt (0.984 g), triethylamine (0.257 g) and chlorobenzene (10 ml), Boc-Phe (0.997 g) and HOBt monohydrate (0.702 g) were added, and the resulting mixture was cooled with ice. Then, EDC hydrochloride (0.835 g) was added thereto, and the resulting mixture was stirred for 2 hours. Subsequently, the temperature of the mixture was raised to room temperature and the mixture was stirred for 1 hour for a condensation reaction (reaction conversion ratio: 99.7%).

The pH of the aqueous layer obtained by washing with 5% aqueous sodium carbonate solution (10 ml) after the reaction was 8.5, and the content of Boc-Phe-Obt as the active ester in the obtained organic layer was 7.9% and the content of Boc-Phe as the acid component therein was 3.8%. The pH of the aqueous layer obtained by repeating said procedure one more time was 10.5, and the content of Boc-Phe-OBt in the obtained organic layer was 1.8% and the content of Boc-Phe therein was 3.6%. The pH of the aqueous layer obtained by further repeating said procedure one more time was 11.0, and the content of Boc-Phe-OBt in the obtained organic layer was 0.1% and the content of Boc-Phe therein was 1.6%.

The thus obtained organic layer was washed once with water (20 ml) and then washed with 10% aqueous citric acid solution (10 ml). Then, saturated brine (10 ml) and water (10 ml) were added thereto for washing, thereby an organic layer (12.268 g) was obtained. The purity of the target Boc-Phe-Leu-OBt was 93%, and the extraction ratio was 99%.

Example 9

Synthesis of Boc-Phe-Leu-OBn with chlorobenzene-DBF Solvent

To the solution composed of Leu-OBn·TsOH salt (4.00 g), triethylamine (1.08 g), chlorobenzene (40 ml) and DBF (10 ml), Boc-Phe (4.04 g) and HOBt monohydrate (2.81 g) were added, and the resulting mixture was cooled with ice. Then, EDC hydrochloride (3.53 g) was added thereto, and the resulting mixture was stirred for 2 hours. Subsequently, the temperature of the mixture was raised to room temperature and the mixture was stirred for 1 hour for a condensation reaction (reaction conversion ratio: 100.0%).

The pH of the aqueous layer obtained by diluting the reaction mixture with chlorobenzene (15 ml) after the reaction and adding 5% aqueous sodium carbonate solution (40 ml) and saturated brine (20 ml) thereto for washing was 8.3, and the content of Boc-Phe-OBt as the active ester in the obtained organic layer was 9.5% and the content of Boc-Phe as the acid component therein was 1.2%. The pH of the aqueous layer obtained by repeating this washing procedure with 5% aqueous sodium carbonate solution and saturated brine three more times was 11.1, and the content of Boc-Phe-OBt in the obtained organic layer was 0.8% and the content of Boc-Phe therein was 0.03%.

The thus obtained organic layer was washed by adding water (20 ml) and saturated brine (40 ml) thereto, thereby an organic layer (67.34 g) was obtained. The purity of the target Boc-Phe-Leu-OBn was 98%, and the extraction ratio was 98%. Further, the water content of the organic layer was 0.37%. After this organic layer (61.98 g) was subjected to dehydration and condensation under reduced pressure, the resulting substance was diluted with chlorobenzene, thereby a dehydrated solution (53.23 g) was obtained. The water content of the solution was 0.03%.

Example 10

Synthesis of Boc-Gly-Phe-Leu-OBn with chlorobenzene-DBF Solvent

To the dehydrated solution (49.11 g) containing Boc-Phe-Leu-OBn obtained in Example 9, methanesulfonic acid (8.30 g, 10 equivalents) was added at room temperature, and the resulting mixture was stirred at room temperature for 10 hours, thereby the Boc group was removed (reaction conversion ratio: 99.8%). After the reaction, 10% aqueous sodium carbonate solution (50 ml) and saturated brine (5 ml) were added thereto and the resulting mixture was stirred for 15 minutes, and then, the aqueous layer was separated off. After Boc-Gly (2.26 g, 1.5 equivalents) and HOBt monohydrate (2.37 g, 1.8 equivalents) were added to the thus obtained chlorobenzene solution of Phe-Leu-OBn, the reaction solution was cooled with ice. Then, EDC hydrochloride (2.96 g, 1.8 equivalents) was added thereto, and the resulting mixture was stirred for 2 hours. Subsequently, the temperature of the mixture was raised to room temperature and the mixture was stirred for 10 hours for a condensation reaction (reaction conversion ratio: 99.9%).

The pH of the aqueous layer obtained by washing by adding 5% aqueous sodium carbonate solution (34 ml) and saturated brine (17 ml) after the reaction was 7.9, and the content of Boc-Gly-OBt as the active ester in the obtained organic layer was 0.1% and Boc-Gly as the acid component was not detected. In the organic layer obtained by the washing procedure with 5% aqueous sodium carbonate solution and saturated brine one more time, Boc-Gly-OBt and Boc-Gly were not detected. After the organic layer was washed once with saturated brine (17 ml), 5% aqueous potassium hydrogen sulfate solution (17 ml) and saturated brine (34 ml) were added thereto for washing. Then, the organic layer was washed with saturated brine (34 ml), and further washed well with chlorobenzene (15 ml), thereby an organic layer (63.90 g) was obtained. The purity of Boc-Gly-Phe-Leu-OBn was 91%, and the extraction ratio was 99.6%. After this organic layer (59.95 g) was subjected to dehydration-ondensation under reduced pressure, the resulting substance was diluted with chlorobenzene, thereby a dehydrated solution (46.28 g) was obtained. The water content of the solution was 0.06%.

Example 11

Synthesis of Boc-Gly-Gly-Phe-Leu-OBn (SEQ ID NO: 1) with chlorobenzene-DBF Solvent A dehydrated solution (43.94 g) containing Boc-Gly-Phe-Leu-OBn obtained by the same procedure to Example 10 was diluted with dichloromethane, thereby a dichloromethane solution (137.01 g) containing Boc-Gly-Gly-Phe-Leu-OBn (SEQ ID NO: 1) was obtained. The purity of the target Boc- Gly-Gly-Phe-Leu-OBn (SEQ ID NO: 1) was 87%, and the extraction ratio was 100%. The water content thereof was 0.09%.

Example 12

Crystallization of Boc-Gly-Gly-Phe-Leu-OBn (SEQ ID NO: 1) with chlorobenzene-DBF Solvent When the dichloromethane solution (35.41 g) containing Boc-Gly-Gly-Phe-Leu-OBn (SEQ ID NO: 1) (purity: 87%) obtained in Example 11 was cooled with ice while being vigorously stirred, a solid was deposited. After the mixture was allowed to mature by stirring for 1 hour under ice-cooling, the deposited solid was collected by filtration, washed with hexane (100 ml) and dried under vacuum, thereby a white solid (0.68 g) was obtained. The purity of the target Boc-Gly-Gly-Phe-Leu-OBn (SEQ ID NO: 1) was 95%, and the crystallization yield was 71%.

As a result of HPLC determination using the obtained crystal as a reference standard, the yield of Boc-Gly-Gly-Phe-Leu-OBn (SEQ ID NO: 1) obtained in Examples 9 to 10, relative to the Leu-OBn•TsOH salt, was 82%.

Example 13

Synthesis of Boc-Tyr(Bn)-Gly-Gly-Phe-Leu-OBn (SEQ ID NO: 4) with dichloromethane-DBF Solvent The dichloromethane solution (57.74 g) containing Boc-Gly-Gly-Phe-Leu-OBn (SEQ ID NO: 1) obtained in Example 11 was subjected to dehydration-condensation under reduced pressure, thereby a dehydrated solution (34.90 g) was obtained. The water content was 0.04%. To the thus obtained dehydrated solution (30.02 g) containing Boc-Gly-Gly-Phe-Leu-OBn (SEQ ID NO: 1), methanesulfonic acid (4.70 g) was added at room temperature, and the resulting mixture was stirred at room temperature for 10 hours, thereby the Boc group was removed (reaction conversion ratio: 100.0%). After the reaction, the resulting mixture was condensed under reduced pressure, thereby a condensed liquid (12.82 g) was obtained. To this condensed liquid, sodium carbonate (3.5 g) and water (20 ml) were added, and the resulting mixture was stirred for 15 minutes. Then, the aqueous layer was separated off. After Boc-Tyr(Bn) (1.502 g) and HOBt monohydrate (0.750 g) were added to the thus obtained dichloromethane solution of Gly-Gly-Phe-Leu-OBn (SEQ ID NO: 3), the reaction solution was cooled with ice. Subsequently, EDC hydrochloride (0.911 g) was added thereto, and the resulting mixture was stirred for 2 hours. Then, the temperature of the mixture was raised to room temperature and the mixture was stirred for 10 hours for a condensation reaction (reaction conversion ratio: 100.0%).

The pH of the aqueous layer obtained by washing by adding 5% aqueous sodium carbonate solution (12 ml) and water (6 ml) to the reaction mixture after the reaction was 9.3, and the content of Boc-Tyr (Bn)-OBt as the active ester in the obtained organic layer was 0.3% and the content of Boc-Tyr (Bn) as the acid component therein was 16.6%. The pH of the aqueous layer obtained by washing the thus obtained organic layer with 5% aqueous sodium carbonate solution (12 ml) and then further washing with water (12 ml) was 10.6, and the content of Boc-Tyr(Bn)-OBt in the obtained organic layer was 0.2% and the content of Boc-Tyr(Bn) therein was 2.5%.

When 5% aqueous potassium hydrogen sulfate solution (12 ml) was added to the thus obtained organic layer and the resulting mixture was stirred, a solid was deposited. After the mixture was allowed to mature by stirring at room temperature for 1 hour, the deposited solid was collected by filtration, washed with dichloromethane (30 ml) and dried under vacuum, thereby a white solid (0.622 g) was obtained. The purity of the target Boc-Tyr(Bn)-Gly-Gly-Phe-Leu-OBn (SEQ ID NO: 4) was 99%, the crystallization yield was 37%, and the acquisition yield relative to the Leu-OBn•TsOH salt was 27%. Further, the content of Boc-Tyr(Bn)-OBt in the obtained organic layer was less than 0.1%, and Boc-Tyr(Bn) therein was not detected.

On the other hand, the obtained filtrate and the washing liquid were combined, and the aqueous layer was separated off. Further, the remaining organic layer was washed with saturated brine (34 ml), thereby a dichloromethane solution (41.78 g) was obtained. The purity of Boc-Tyr (Bn)-Gly-Gly-Phe-Leu-OBn (SEQ ID NO: 4) was 78%, the extraction ratio was 99.5%, and the yield relative to the Leu-OBn•TsOH salt was 45%. Further, the content of Boc-Tyr(Bn)-OBt in the obtained organic layer was 0.3%, and the content of Boc-Tyr (Bn) therein was 7.4%.

Example 14

Synthesis of Tyr (Bn)-Gly-Gly-Phe-Leu-OBn (SEQ ID NO: 2) with chlorobenzene-DBF Solvent, and Removal of Tyr(Bn) Acid Salt The white solid (0.183 g) obtained in Example 13 and dichloromethane (12.28 g) were mixed. After the resulting mixture was subjected to dehydration-condensation under reduced pressure, the resulting substance was diluted with chlorobenzene, thereby a dehydrated solution (8.95 g) of which contents of Boc-Tyr (Bn)-OBt and of Boc-Tyr(Bn) were respectively 0.2% and 4.5% was obtained. To this dehydrated solution, methanesulfonic acid (1.38 g, 18 equivalents) was added at room temperature, and the resulting mixture was stirred at room temperature for 18 hours, thereby a solid was deposited as the reaction proceeded. The content of Tyr(Bn) in the obtained reaction mixture as a slurry was 11.1%.

After the reaction mixture as a slurry was allowed to mature by stirring for 1 hour, the deposited solid was filtered, washed with chlorobenzene (3 ml), and then dried under vacuum. The thus obtained white solid (0.06 g) contained Tyr (Bn) as a main component. The purity of Tyr(Bn) was 82%, and the content of Tyr(Bn)-Gly-Gly-Phe-Leu-OBn (SEQ ID NO: 2) was 15%, which corresponds to the yield of 1%.

On the other hand, the filtrate and the washing liquid were well washed with chlorobenzene (5 ml) and then combined with each other, thereby a clear solution was obtained. When 10% aqueous sodium carbonate solution (12 ml) was added to the solution, a solid was deposited. After the mixture was allowed to mature by stirring at room temperature for 1 hour and then under ice-cooling for 1 hour, the deposited solid was filtered, and sequentially washed with chlorobenzene (2 ml) and water (2 ml), and dried under vacuum, thereby a white solid was obtained. The purity of the target Tyr(Bn)-Gly-Gly-Phe-Leu-OBn (SEQ ID NO: 2) was 88%, and the content of Tyr(Bn) was 4.9%. Further, the crystallization yield was 88%, and the acquisition yield relative to the Leu-OBn•TsOH salt was 58%.

Example 15

Synthesis of Boc-Tyr(Bn)-Gly-Gly-Phe-Leu-OBn (SEQ ID NO: 4) with chlorobenzene-DBF Solvent After the dichloromethane solution (18.22 g) containing Boc-Gly-Gly-Phe-Leu-OBn (SEQ ID NO: 1) obtained in Example 11 was subjected to dehydration-condensation under reduced pressure, the resulting substance was diluted with chlorobenzene, thereby a dehydrated solution (5.48 g) was obtained. To the dehydrated solution, methanesulfonic acid (1.74 g, 18 equivalents) was added at room temperature, and the resulting mixture was stirred at room temperature for 5 hours, thereby the Boc group was removed (reaction conversion ratio: 100.0%). After the reaction, 10% aqueous sodium carbonate solution (15 ml) was added thereto, and the resulting mixture was stirred for 15 minutes. Then, the mixture was condensed under reduced pressure thereby distilling off chlorobenzene until the total amount of the solution was 18.35 g. After saturated brine (2 ml) was added to the solution and the mixture was stirred for 15 minutes, the aqueous layer was separated off. After Boc-Tyr(Bn) (0.554 g) and HOBt monohydrate (0.273 g) were added to the obtained chlorobenzene solution of Gly-Gly-Phe-Leu-OBn (SEQ ID NO: 3), the reaction solution was cooled with ice. Then, EDC hydrochloride (0.353 g) was added thereto, and the resulting mixture was stirred for 2 hours. Subsequently, the temperature of the mixture was raised to room temperature and the mixture was stirred for 13 hours for a condensation reaction (reaction conversion ratio: 100.0%).

The pH of the aqueous layer obtained by washing by adding 5% aqueous sodium carbonate solution (5 ml) and saturated brine (5 ml) to the reaction mixture after the reaction was 8.5, and the content of Boc-Tyr(Bn)-OBt as the active ester in the obtained organic layer was 0.8% and the content of Boc-Tyr(Bn) as the acid component was 30.3%.

The pH of the aqueous layer obtained by the washing procedure with 5% aqueous sodium carbonate solution and saturated brine one more time was 9.6, and the content of Boc-Tyr(Bn)-OBt in the obtained organic layer was 0.2% and the content of Boc-Tyr(Bn) was 0.1%. Subsequently, the obtained organic layer was washed once with saturated brine (15 ml) and then washed by adding 5% aqueous potassium hydrogen sulfate solution (5 ml) and saturated brine (15 ml) thereto. Then, saturated brine (15 ml), water (15 ml) and chlorobenzene (8 ml) were added to the organic layer, and the resulting mixture was condensed under reduced pressure, thereby distilling off chlorobenzene until the total amount of the solution was 7.29 g. As a result, a solid was deposited. When chlorobenzene (10 ml) and water (15 ml) were added thereto, and the resulting mixture was allowed to mature at room temperature for 1 hour, a homogenous slurry was formed. Then, after the slurry was allowed to mature by stirring for 1 hour under ice-cooling, the deposited solid was filtered, and sequentially washed with chlorobenzene (2 ml) and water (2 ml), and then dried under vacuum, thereby a white solid was obtained. The purity of the target Boc-Tyr (Bn)-Gly-Gly-Phe-Leu-OBn (SEQ ID NO: 4) was 92%, and the content of Tyr(Bn) was 2.1%. Further, the crystallization yield was 93%, and the acquisition yield relative to the Leu-OBn•TsOH salt was 64%.

On the other hand, when the filtrate and the washing liquid were well washed with water (2 ml) and chlorobenzene (2 ml), and then combined with each other, the solution was separated into two clear layers. The aqueous layer was separated off, and an organic layer (18.91 g) was obtained. The purity of Boc-Tyr(Bn)-Gly-Gly-Phe-Leu-OBn (SEQ ID NO: 4) was 71%, and the extraction ratio was 100%, and the yield relative to the Leu-OBn•TsOH salt was 4%.

Example 16

Synthesis of Boc-Leu-Arg(Ts)-Pro-NEtBn

Boc-Arg (Ts)-Pro-NEtBn was prepared by a similar procedure to Example 1 from Boc-Pro-NEtBn and Boc-Arg(Ts). To the solution composed of the compound (1.00 g), chlorobenzene (5.8 ml) and DBF (1.5 ml), methanesulfonic acid (1.41 g, 9.8 equivalents) was added at room temperature, and the resulting mixture was stirred at room temperature for 24 hours, thereby the Boc group was removed (reaction conversion ratio: 100.0%). After the reaction, 10% aqueous sodium carbonate solution (12 ml) was added thereto, and the resulting mixture was stirred for 15 minutes for neutralization. Then, the aqueous layer was separated off, thereby a solution containing Arg(Ts)-Pro-NEtBn (8.58 g) was obtained.

After Boc-Leu monohydrate (0.54 g) and HOBt monohydrate (0.41 g) were added to the thus obtained solution (8.28 g), the reaction solution was cooled with ice. Then, EDC hydrochloride (0.51 g) and water (1.5 ml) were added thereto, and the resulting mixture was stirred for 2 hours. Subsequently, the temperature of the mixture was raised to room temperature and the mixture was stirred for 0.5 hour for a condensation reaction (reaction conversion ratio: 99.9%).

After the reaction, 5% aqueous sodium carbonate solution (6 ml) and saturated brine (6 ml) were added thereto. The resulting mixture was stirred for 15 minutes, and then, the aqueous layer was separated off. The pH of the aqueous layer at the time was 7.9, and the content of Boc-Leu-OBt as the active ester in the obtained organic layer was 6.6%, and the content of Boc-Leu as the acid component was 0.1%. The pH of the aqueous layer obtained by repeating said procedure one more time was 10.1, and the content of Boc-Leu-OBt in the obtained organic layer was 5.5% and Boc-Leu was not detected. The pH of the aqueous layer obtained by repeating said procedure five more time was 10.6, and the content of Boc-Leu-OBt in the obtained organic layer was 1.1%.

The obtained organic layer was washed once with saturated brine (6 ml), and then washed by adding 5% aqueous potassium hydrogen sulfate solution (6 ml) and saturated brine (12 ml), and was condensed under reduced pressure, thereby a condensed product (7.65 g) was obtained. The purity of the target Boc-Leu-Arg(Ts)-Pro-NEtBn was 91%, and the yield was 91%.

Example 17

Synthesis of Boc-D-Leu-Leu-Arg(Ts)-Pro-NEtBn

To the condensed product (7.442 g) containing Boc-Leu-Arg(Ts)-Pro-NEtBn obtained in Example 16, methanesulfonic acid (1.329 g, 10 equivalents) was added at room temperature, and the resulting mixture was stirred at room temperature for 6 hours to remove the Boc group (reaction conversion ratio: 100.0%). After the reaction, 10% aqueous sodium carbonate solution (12 ml) was added thereto, and the resulting mixture was stirred for 15 minutes for neutralization. Then, the aqueous layer was separated off, and the resulting organic layer was condensed under reduced pressure, thereby a condensed product (2.283 g) containing Leu-Arg(Ts)-Pro-NEtBn was obtained.

After a chlorobenzene solution of Boc-D-Leu (4.583 g, concentration: 10.1%) and HOBt monohydrate (0.372 g) were added to the obtained condensed product (2.226 g), the reaction solution was cooled with ice. Then, EDC hydrochloride (0.453 g) and water (1.3 ml) were added thereto, and the resulting mixture was stirred for 2 hours. Subsequently, the temperature of the mixture was raised to room temperature and the mixture was stirred for 13 hours for a condensation reaction (reaction conversion ratio: 100.0%).

After the reaction, 5% aqueous sodium carbonate solution (5 ml), water (5 ml) and saturated brine (10 ml) were added thereto, and the resulting mixture was stirred for 15 minutes, and then, the aqueous layer was separated off. The pH of the aqueous layer at this time was 7.2, and the content of Boc-D-Leu-OBt as the active ester in the obtained organic layer was 5.3% and the content of Boc-D-Leu as the acid component therein was 0.004%. The pH of the aqueous layer obtained by repeating said procedure one more time was 9.8, and the content of Boc-D-Leu-OBt in the obtained organic layer was 4.3% and Boc-D-Leu was not detected. The pH of the aqueous layer obtained by repeating said procedure seven more time was 10.7, and the content of Boc-D-Leu-OBt in the obtained organic layer was 0.8%.

After the obtained organic layer was washed once by adding 5% aqueous potassium hydrogen sulfate solution (5 ml) and saturated brine (15 ml) and then washed with saturated brine (5 ml), the organic layer was condensed under reduced pressure, thereby a condensed product (8.024 g) was obtained. The purity of the target Boc-D-Leu-Leu-Arg(Ts)-Pro-NEtBn was 93%, and the yield was 99%.

Example 18

Synthesis of Boc-Tyr(Bn)-D-Leu-Leu-Arg(Ts)-Pro-NEtBn

To the condensed product (3.782 g) containing Boc-D-Leu-Leu-Arg(Ts)-Pro-NEtBn obtained in Example 17, methanesulfonic acid (0.597 g, 9.9 equivalents) was added at room temperature, and the resulting mixture was stirred at room temperature for 15 hours to remove the Boc group (reaction conversion ratio: 100.0%). After the reaction, 10% aqueous sodium carbonate solution (5 ml) was added thereto, and the resulting mixture was stirred for 15 minutes for neutralization. Then, the aqueous layer was separated off, and the resulting organic layer was condensed under reduced pressure, thereby a condensed product (3.584 g) containing D-Leu-Leu-Arg(Ts)-Pro-NEtBn was obtained.

After Boc-Tyr(Bn) (0.338 g) and HOBt monohydrate (0.167 g) were added to the obtained condensed product (3.444 g), the reaction solution was cooled with ice. Then, EDC hydrochloride (0.209 g) and water (0.6 ml) were added thereto, and the resulting mixture was stirred for 2 hours. Subsequently, the temperature of the mixture was raised to room temperature and the mixture was stirred for 0.5 hour for a condensation reaction (reaction conversion ratio: 99.9%).

After the reaction, 5% aqueous sodium carbonate solution (2.5 ml) and saturated brine (2.5 ml) were added thereto, and the resulting mixture was stirred for 30 minutes. The pH of the aqueous layer at this time was 8.4, and the content of Boc-Tyr(Bn)-OBt as the active ester in the organic layer which was obtained by layer separation by leaving the mixture stand without separating off the aqueous layer was 5.6% and the content of Boc-Tyr(Bn) as the acid component therein was 26%. When 48% aqueous sodium hydroxide solution (0.210 g) was added to this reaction mixture with stirring, the pH of the reaction mixture was raised to 11.4 once; however, at 10 minutes thereafter, the pH was decreased to 10.8. The pH of the mixture was further measured every 10 minutes. As a result, the pH remained 10.8. The content of Boc-Tyr(Bn)-OBt in the organic layer obtained by separating off the aqueous layer was 0.2%, and the content of Boc-Tyr(Bn) therein was 39%.

The thus obtained organic layer was washed once with saturated brine (5 ml) and then washed once by adding 5% aqueous potassium hydrogen sulfate solution (2.5 ml) and saturated brine (2.5 ml), and then washed with saturated brine (2.5 ml). The obtained organic layer was condensed under reduced pressure, and was subjected to solvent replacement with chlorobenzene (4 ml), thereby a condensed product (7.385 g) was obtained. The purity of the target Boc-Tyr(Bn)-D-Leu-Leu-Arg(Ts)-Pro-NEtBn was 66%, and the content of Boc-Tyr (Bn) therein was 33%. Further, the yield was 97%.

The invention claimed is:

1. A method of producing a peptide by a liquid phase synthesis method, comprising steps of:

Step A: reacting the active ester of the acid of a first amino acid or a first peptide with the amine of a second amino acid or a second peptide to obtain a first reaction mixture comprising an intermediate peptide, wherein the amine of the first amino acid or the first peptide has a protecting group such that the intermediate peptide has an N-terminal amine protecting group;

Step B: purifying the intermediate peptide contained in the first reaction mixture obtained in Step A, wherein the purification is performed by using an amide-type solvent immiscible with water or a mixed solvent containing the amide-type solvent immiscible with water and a halogenated hydrocarbon-type solvent, and by separating the solvent layer containing the intermediate peptide from an aqueous layer;

Step C: removing the N-terminal amine protecting group of the intermediate peptide obtained in Step B to form a second reaction mixture; and Step D: purifying the intermediate peptide contained in the second reaction mixture, if necessary.

2. The method according to claim 1, wherein the amide-type solvent immiscible with water is selected from the group consisting of N,N-dibutylformamide, N,N-dipropylformamide, N,N-dibutylacetamide and N,N-dipropylacetamide.

3. The method according to claim 1, wherein the amide-type solvent immiscible with water is used in Steps A, B and C.

4. The method according to claim 1, wherein the acid of the second amino acid or the second peptide in Step A has a protecting group such that the intermediate peptide formed in Step B has a C-terminal acid protecting group.

5. The method according to claim 1, wherein Step D is conducted under an acidic condition for crystallization.

6. The method according to claim 1, wherein the intermediate peptide in Step D is purified by crystallization.

7. The method according to claim 1, wherein a mixed solvent containing the amide-type solvent immiscible with water and a halogenated hydrocarbon-type solvent is used.

* * * * *